(12) United States Patent
Prince et al.

(10) Patent No.: US 8,427,636 B2
(45) Date of Patent: Apr. 23, 2013

(54) CUVETTE FOR OPHTHALMIC LENS

(75) Inventors: Simon Prince, Newbury Park, CA (US);
Michael Sherwood, Agoura, CA (US);
Robert E. Fischer, Westlake Village, CA (US); Syed Tariq Shafaat, Marina Del Rey, CA (US); Shawn Mulcahey, Moorpark, CA (US); Paul Hudson, Newbury Park, CA (US); Greg Moeller, Moorpark, CA (US); Gregory A. Williby, St. Johns, FL (US); Russell T. Spaulding, St. Johns, FL (US); John C. Hootman, Orange Park, FL (US); Russell J. Edwards, Jacksonville, FL (US); John Edward Greivenkamp, Jr., Tucson, AZ (US)

(73) Assignees: Johnson & Johnson Vision Care, Inc, Jacksonville, FL (US); Arizona Board of Regents on Behalf of the University of Arizona, Tucson, AZ (US)

( * ) Notice: Subject to any disclaimer, the term of this patent is extended or adjusted under 35 U.S.C. 154(b) by 504 days.

(21) Appl. No.: 11/962,662

(22) Filed: Dec. 21, 2007

(65) Prior Publication Data
US 2008/0151236 A1    Jun. 26, 2008

Related U.S. Application Data

(60) Provisional application No. 60/871,319, filed on Dec. 21, 2006.

(51) Int. Cl.
*G01N 1/10* (2006.01)

(52) U.S. Cl.
USPC .................................................... 356/246

(58) Field of Classification Search .......... 356/246
See application file for complete search history.

(56) References Cited

U.S. PATENT DOCUMENTS

| 3,555,284 | A | * | 1/1971 | Anderson | 436/45 |
| 3,606,997 | A | * | 9/1971 | Guckel | 422/26 |
| 3,942,952 | A | | 3/1976 | Atwood | |
| 4,313,735 | A | | 2/1982 | Yamashita et al. | |
| 5,099,987 | A | | 3/1992 | Bieri | |

(Continued)

FOREIGN PATENT DOCUMENTS

| CA | 1233976 A1 | 3/1988 |
| EP | 0604173 A | 6/1994 |

(Continued)

OTHER PUBLICATIONS

Hecht, E., Optics, Second Edition, Addison-Wesley, Reading, MA 1987, pp. 346-361.

(Continued)

*Primary Examiner* — Tarifur Chowdhury
*Assistant Examiner* — Jonathon Cook
(74) *Attorney, Agent, or Firm* — Woodcock Washburn LLP

(57) ABSTRACT

Modified MZ (Mach-Zender) interferometers are utilized to analyze the transmitted, aspherical wavefront of an ophthalmic lens by mounting the lens in a cuvette having a rotatable carousel that can hold multiple lenses. Fresh, temperature controlled, saline solution is circulated about the lenses, and the cuvette is positioned in a vertical test arm of the interferometer configuration. Reverse raytracing is utilized to remove aberrations induced into the wavefront as it is imaged from immediately behind the lens to the detector of the interferometer.

19 Claims, 21 Drawing Sheets

U.S. PATENT DOCUMENTS

| | | | |
|---|---|---|---|
| 5,151,752 | A | 9/1992 | Oono et al. |
| 5,311,426 | A * | 5/1994 | Donohue et al. ............. 73/1.02 |
| 5,439,642 | A * | 8/1995 | Hagmann et al. ............. 422/22 |
| 5,518,686 | A * | 5/1996 | Masterson et al. ............. 422/63 |
| 5,818,573 | A | 10/1998 | Lafferty et al. |
| 5,963,318 | A | 10/1999 | Held |
| 6,047,082 | A * | 4/2000 | Rhody et al. ............. 382/141 |
| 6,597,442 | B2 | 7/2003 | Maeda et al. |
| 6,626,535 | B2 * | 9/2003 | Altmann ............. 351/177 |
| 6,765,661 | B2 | 7/2004 | Biel et al. |
| 6,909,503 | B2 | 6/2005 | Baske et al. |
| 2004/0008877 | A1 | 1/2004 | Leppard et al. |

FOREIGN PATENT DOCUMENTS

| | | |
|---|---|---|
| EP | 1544601 A1 | 6/2005 |
| JP | 05234971 | 10/1993 |
| JP | 11037937 | 2/1999 |
| WO | 99/26052 A | 5/1999 |
| WO | WO 03/050470 | 6/2003 |
| WO | WO 2006091415 | 8/2006 |

OTHER PUBLICATIONS

Greivenkamp, J. E. et al., "Phase Shifting Interferometers", in Optical Shop Testing, Second Edition, D. Malacara, ed., Ch. 14, pp. 501-598, John Wiley & Sons, New York, 1992.

Born, M. et al., Principles of Optics, Sixth (Corrected) Edition, Cambridge University Press, Cambridge, UK, 1980, pp. 312-316.

Gappinger, R.O. et al., "Iterative Reverse Optimization Procedure for Calibration of Aspheric Wave-Front Measurements on a Nonull Interferometer", Applied Optics, Sep. 20, 2004, 43(27), 5152-5161, XP002479854.

Greivenkamp, J.E. et al., "Design of Nonnull Interferometer for Aspheric Wave Fronts", Applied Optics, Sep. 20, 2004, 43(27), 5143-5151, XP002479855.

Williby, G.A. et al., "Interferometric Testing of Soft Contact Lenses", Proceedings of the SPIE—The International Society for Optical Engineering, 2003, 5180, 329-339, XP002479853.

Wyant et al., "Basic Wavefront Aberration Theory for Optical Metrology", Applied Optics and Optical Engineering, 1992, 11, Ch. 1, 28-39.

* cited by examiner

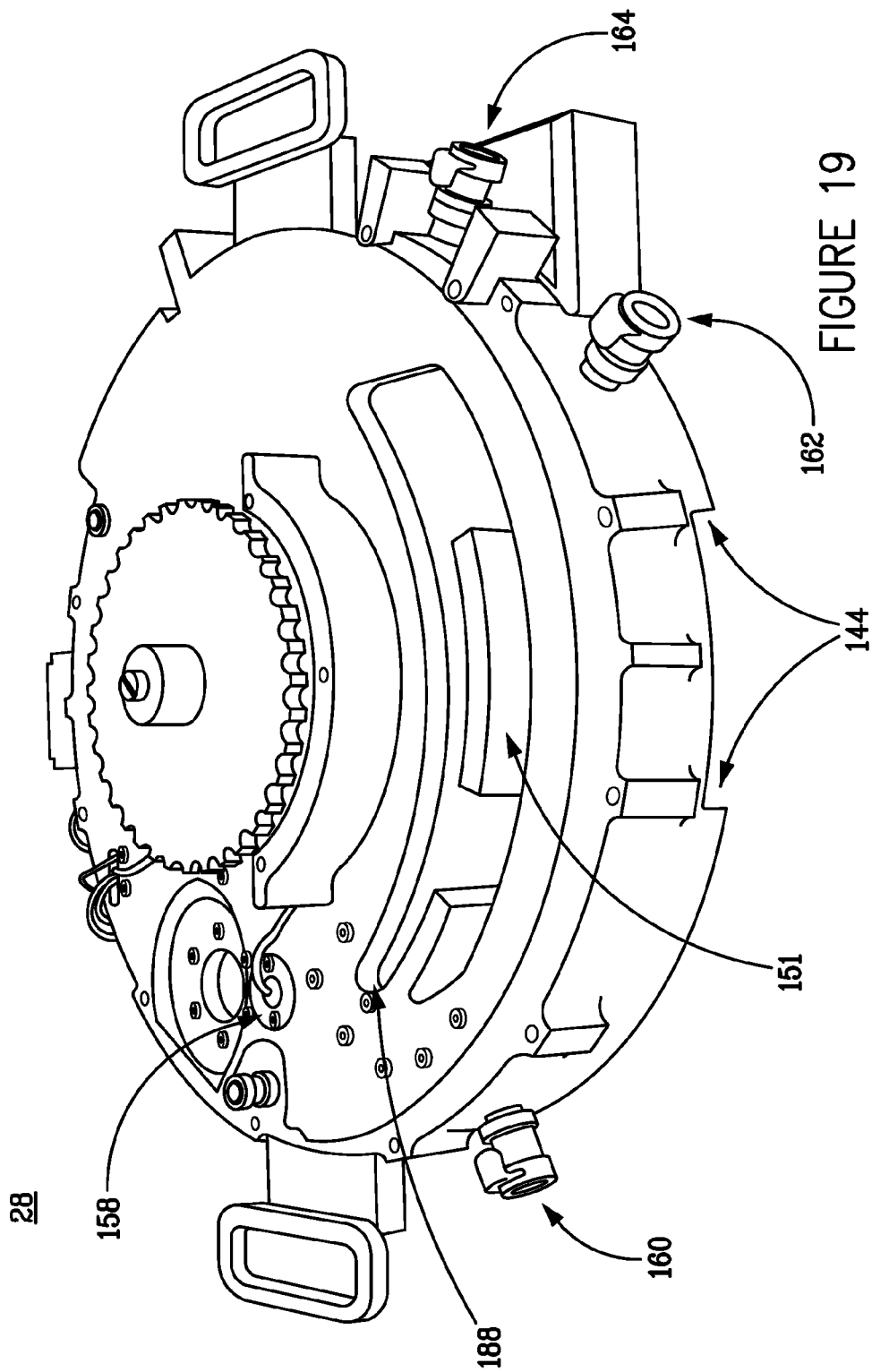

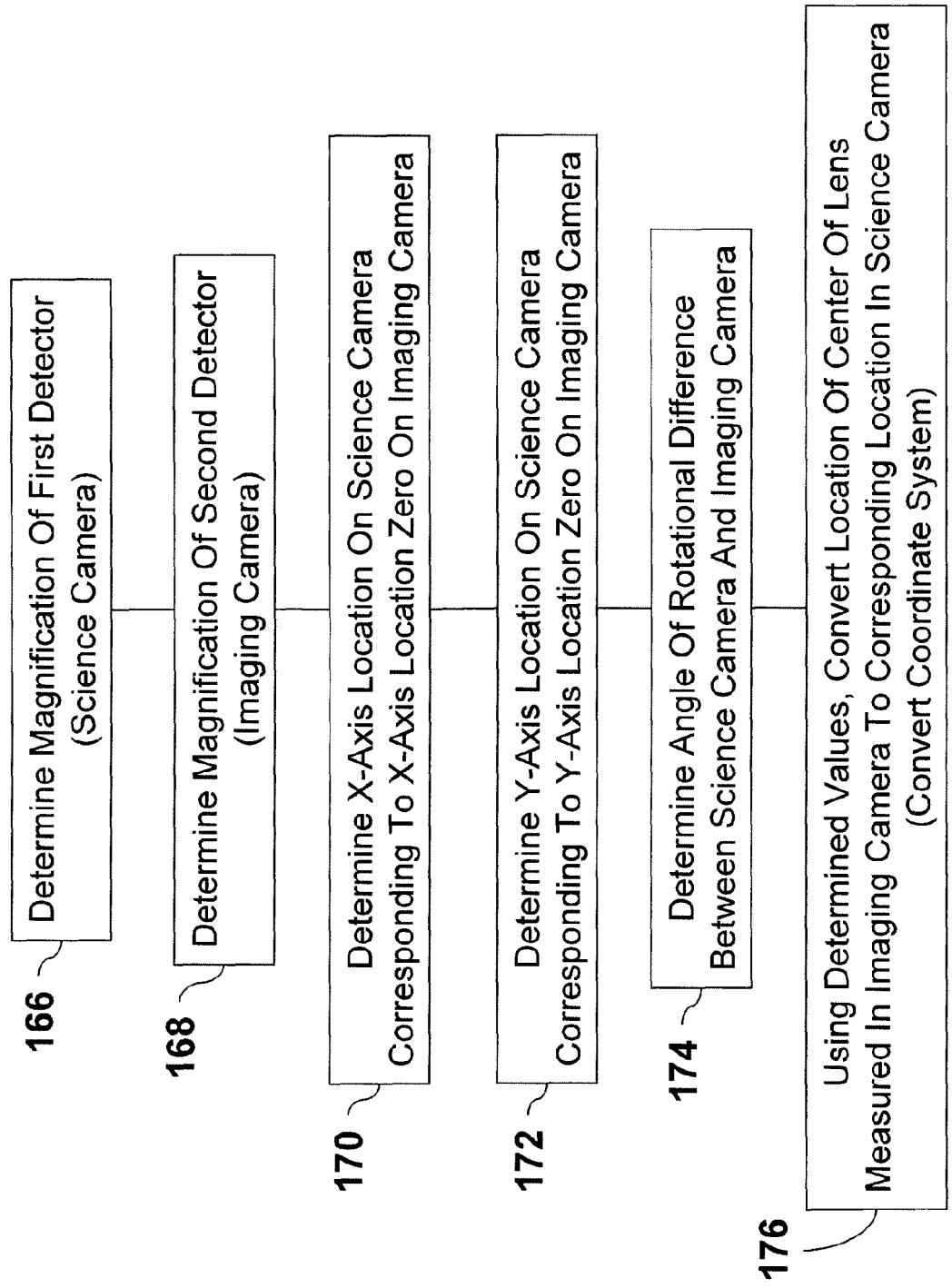

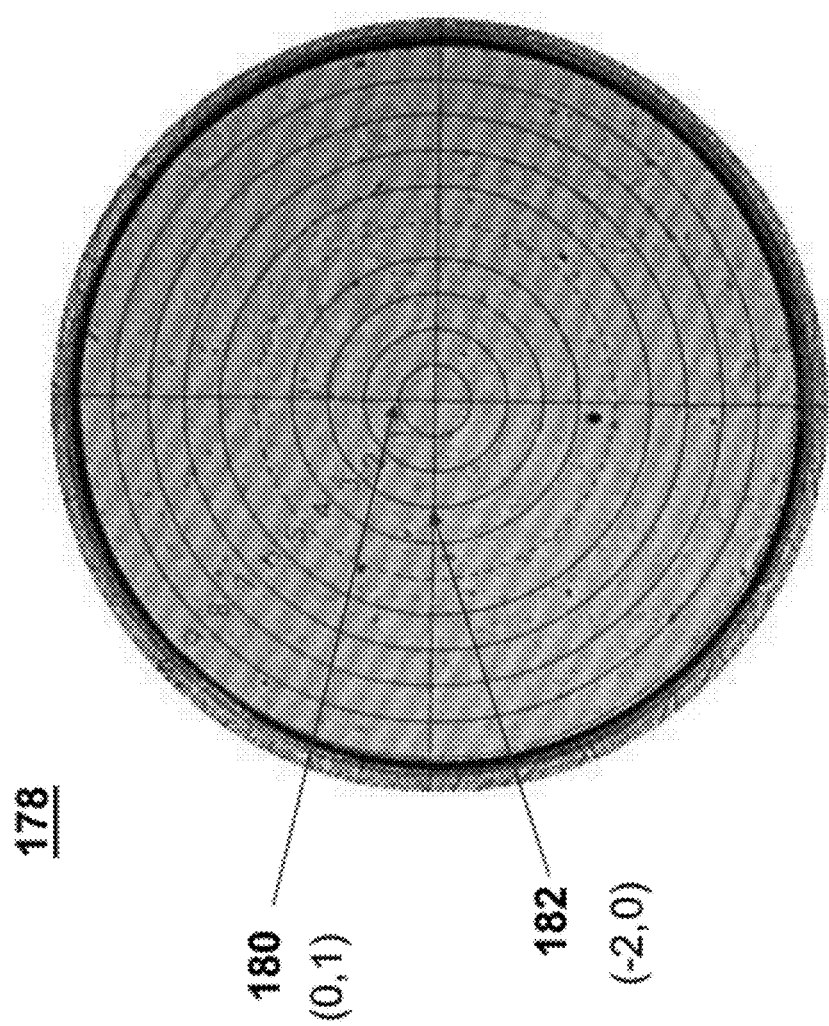

CUVETTE FOR OPHTHALMIC LENS

CROSS REFERENCE TO RELATED APPLICATIONS

The present application claims benefit to U.S. Provisional Patent Application No. 60/871,319, titled "INTERFEROMETRY TESTING OF LENSES, AND SYSTEMS AND DEVICES FOR SAME," filed Dec. 21, 2006, which is hereby incorporated by reference in its entirety.

TECHNICAL FIELD

The technical field relates generally to optics and more specifically a systems and methods for testing optical lenses, vessels for holding the lenses, and methods for analyzing optical characteristics of the lenses.

BACKGROUND

The contact lens industry has undergone rapid advancements toward higher levels of visual correction. Manufacturers are progressing toward providing contact lenses that are designed to match a patient's refractive correction and fit. By moving beyond standard spherical lenses, manufacturers will be able to provide contact lens wearers with better visual acuity and overall comfort.

Metrology (measurement) techniques and instrumentation for evaluating lenses, however, have not kept up with the rapid advancement in lens technology. Current metrology, such as methods based on focimeters and moiré deflectometry, lacks the combination of spatial resolution, high sensitivity, and large dynamic range desired to accurately measure more advanced lenses. Current metrology techniques generally are limited to ophthalmic testing of the effective power of a lens and indirect measurements of power by translating a lens until collimation is detected.

SUMMARY

In one aspect, the present invention involves utilization of a modified Mach-Zehnder (MZ) interferometer to analyze the transmitted, aspherical wavefront of an ophthalmic lens. The interferometer is capable of analyzing a wide variety of lens types, such as, for example, spherical, toric, bifocal, and multifocal lenses. In certain embodiments of the invention, lenses are mounted in a cuvette that circulates fresh saline about the lenses and is positioned in a vertical test arm of the interferometer configuration. A technique referred to as reverse raytracing can be utilized to remove aberrations induced into the wavefront as it is imaged.

BRIEF DESCRIPTION OF THE DRAWINGS

The foregoing summary, as well as the following detailed description, is better understood when read in conjunction with the appended drawings. For the purpose of illustrating the use of interferometry for transmitted wavefront testing of lenses, there is shown in the drawings exemplary constructions thereof; however, use of interferometry for transmitted wavefront testing of lenses is not limited to the specific methods and instrumentalities disclosed.

FIG. 19 is a diagram of an enclosed cuvette.

FIG. 20 is a flow diagram of an example process for aligning detectors of an interferometer configuration for obtaining a wavefront of a lens.

FIG. 21 depicts an example target lens used in the alignment of detectors.

DETAILED DESCRIPTION OF ILLUSTRATIVE EMBODIMENTS

The present invention involves obtaining information utilized to evaluate a wide range of ophthalmic lens types by measuring the transmitted wavefront of the lens. In certain embodiments, a Mach-Zehnder interferometer is used with the lenses submersed in saline solution and mounted in a cuvette, or water cell, that circulates fresh saline solution. Testing lenses in a saline solution is believed to mitigate dehydration of the lens, which can change the lens' index of refraction. Removal of induced aberrations can be achieved, for example, by reverse raytracing, wherein the wavefront at the detector is traced back to a location immediately behind the lens. Reverse raytracing facilitates the generation of theoretical wavefronts, which can be used to evaluate performance at the transmitted wavefront level.

Example type of lenses that can be evaluated include hard contact lenses, hard refractive contact lenses, hard diffractive contact lenses, hard hybrid refractive/diffractive contact lenses, soft contact lenses, soft refractive contact lenses, soft diffractive contact lenses, soft hybrid refractive/diffractive contact lenses, hard contact lenses comprising an active pharmaceutical, soft contact lenses comprising an active pharmaceutical, single vision lenses, toric lenses, bifocal contact lenses, multifocal lenses, cosmetically tinted lenses, freeform lenses, an intraocular lenses, intraocular refractive lenses, an intraocular diffractive lenses, intraocular hybrid refractive/diffractive lenses, accommodating lenses, spectacle lenses, refractive spectacle lenses, diffractive spectacle lenses, and hybrid refractive/diffractive spectacle lenses, composite lenses comprising multiple and embedded materials, photochromic lenses, and molds used in the fabrication of the aforementioned lenses. It is to be understood that example lenses should not be limited to the preceding list of example lenses. Those of skill in the art will readily recognize that other types of lenses are applicable and appropriate for evaluation via transmitted wavefront analysis.

Figure 1:
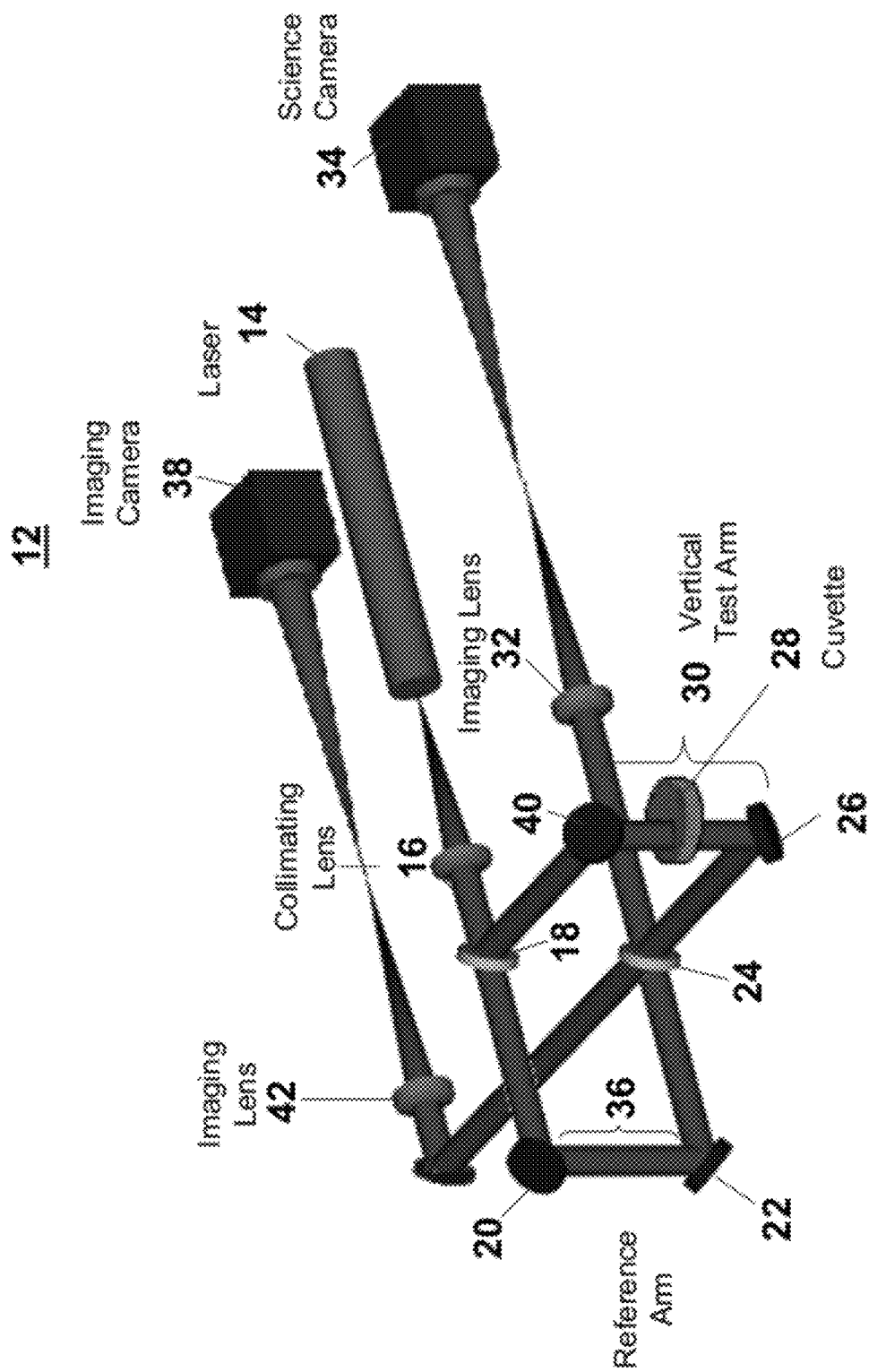
FIG. 1 is a diagram depicting an exemplary interferometer configuration for obtaining a wavefront of a lens.

FIG. 1 is a diagram depicting an exemplary interferometer configuration 12 for obtaining a wavefront of a lens. The interferometer configuration 12 comprises two beam splitters 18, 24 and four mirrors 20, 22, 26, 40 for steering beams of light through the reference arm 36 and the vertical test arm 30. The cuvette 28 is positioned in the vertical test arm 30, and the lens, or lenses, to be tested are placed in the cuvette 28 (lens not shown in FIG. 1). The light source 14, such as a laser for example, produces a coherent beam of light. Coherence is measured in units of length, and in an exemplary embodiment, the coherence of the source 14 is greater than the expected difference in optical path distance of the reference arm 36 path and the vertical test arm 30 path. Light leaving the source 14 is filtered and shaped using a collimating lens 16. The collimated beam of light emanating from the collimating lens 16 is split into two beams using a beam splitter 18 at 45°. In essence, a beam splitter is a special type of mirror wherein 50% of the light is reflected, and the other 50% is transmitted. Thus, 50% of the collimated light beam emanating from the collimating lens 16 is directed, via the beam splitter 18, toward the mirror 40 and the other 50% of the collimated light beam is directed toward the mirror 20.

The beam directed toward the mirror 20 is reflected by that mirror through the reference arm 36. This beam is referred to as the reference beam. The beam directed toward the mirror 40 is also reflected by the mirror 20 through the vertical test arm 30. This beam is referred to as the test beam. The test beam passes through the cuvette 28 and test lens contained therein. Concurrently, the reference beam passes through air, or any appropriate gas, of the reference arm 36. Using another beam splitter 24, the reference beam and test beam are recombined, and interference between the two beams occurs. Two beams emanate from the beam splitter 24. One beam, directed toward imaging lens 42, is indicative of a portion of the test beam that is transmitted through the beam splitter 24 combined with a portion of the reference beam that is reflected from the beam splitter 24. The other beam, directed toward the imaging lens 32, is indicative of a portion of the test beam that is reflected from the beam splitter 24 combined with a portion of the reference beam that is transmitted through the beam splitter 24.

The interference of the beam directed toward the imaging lens 32 is recorded using a camera 34. The camera 34 can comprise any appropriate type of camera, such as a charge coupled device (CCD) camera, a complementary metal-oxide-semiconductor (CMOS) camera, a charge-injection device (CID), or the like, for example. The camera 34 is referred to as the science camera. The imaging lens 32 is placed between the beam splitter 24 and the science camera 34 to image the test lens onto the camera. Thus, the interference recorded by the science camera 34 comprises the image of the interference pattern at the lens under test.

The beam that is directed toward the imaging lens 42 is collected by the camera 38, which is referred to as the imaging camera. The camera 38 can comprise any appropriate type of camera, such as a charge coupled device (CCD) camera, a complementary metal-oxide-semiconductor (CMOS) camera, a charge-injection device (CID), or the like, for example. The light collected by the imaging camera 38 is indicative of the light that is reflected off the beam splitter 24 from the reference arm 22 and the light that is transmitted through the beam splitter 24 from the test arm 30. Utilization of the two cameras 34, 38 provides two views of the lens under test. In an exemplary embodiment, the imaging camera 38 is set to a fixed magnification level that allows the imaging camera 38 to see and record the entire lens under test. Images from the imaging camera 38 are used in the diameter and circularity measurements as well as setting the placement of the analysis aperture within the optical zone of the test lens. The science camera 34 sees the central portion of the optical zone of the test lens. This provides maximum spatial resolution when measuring the transmitted wavefront of the test lens.

The interferometer configuration 12 does not utilize null optics. That is, there are no devices added or removed from the interferometer configuration 12 to remove signal attributable to the interferometer configuration 12. Utilization of null optics would likely require the design of null optics for each lens type, and the wide range of lens types makes this impracticable. Testing in a non-null configuration brings into play at least three design factors of the interferometer configuration 12. First, because the wavefront is collected and captured by the imaging optics (e.g., science camera 34 and imaging camera 38), the parameters of the test wavefront, imaging lens, and detector are matched. Second, the interference incident on the detector is resolved. In an exemplary embodiment, the interference fringes are prohibited from changing in phase by more than pi ($\pi$) per pixel, thereby ensuring that the fringe frequency is less than the Nyquist frequency for the detector. In an alternate embodiment, however, sub-Nyquist interferometry, with its sparse array camera, is utilized to resolve the high frequency interference generated by aspherics in a non-null configuration. Third, the wavefront reconstructed at the detector is calibrated to account for the induced aberrations by the interferometer's 12 imaging optics. The lack of a common path between the reference arm 36 and test arm 30 wavefronts results in different aberrations in each wavefront. An exemplary calibration process for removing the induced aberrations is described below.

In an exemplary embodiment, the interference patterns are digitized and recorded as digital data that is processed to generate the transmitted wavefront for the tested optic (the lens under test). The measured transmitted wavefront is analyzed to determine characteristics of the tested optic such as its diameter, circularity, relative thickness, defects, and ophthalmic prescription.

In an exemplary embodiment, the mirror 38 located at the top of the reference arm 36 comprises a phase shifting capability. The phase shifting capability can be implemented by using any appropriate material such as, for example, lead zirconate titonate ($Pb[Zr_xTi_{1-x}]O_3$), PZT). PZT is a ceramic material comprising ferroelectric and piezoelectric properties. In this embodiment, the mirror 38 is a dynamic component attached to the top reference arm mirror. The PZT material provides a small (fraction of a wavelength) translation to the top mirror 38. This produces a phase shift in the recorded interference pattern. A series of patterns is recorded. Determination of the direction of the phase shift removes the ambiguity of the sign of the test optic's power. For example, in a static interferometer, a +1 D and a −1 D lens would be indistinguishable. Utilizing the mirror 38 with a phase-shifting capability, however, removes this ambiguity.

As shown in FIG. 1, the test arm 30 is vertically oriented. To prevent contact lenses from defecting under their own weight, lenses are mounted in a horizontal orientation within the cuvette 28, which is positioned in the vertical test arm 30. To facilitate a horizontal positioning of the cuvette 28, the two beamsplitters 26, 40 are arranged vertically as shown in FIG. 1. The interferometer configuration 12 provides a vertical beam path for a test lens placed between the periscope mirrors 26, 40. The interferometer configuration 12 preserves equal test path lengths for the reference arm 36 and the test arm 30 while allowing an enclosure, cuvette 28, over the lens under test. As described in more detail below, the cuvette 28 provides a nearly light-tight environment, protects the optics from the saline solution used with the lenses, and blocks the system from external air turbulence.

The diameter of the imaging lenses 32 and 42 are capable of capturing all or substantially all expected wavefronts. The interferometer configuration 12 is capable of testing both positive and negative lenses. With negative lenses, the wavefront after the lens under test diverges, and thus the distance from the lens under test to the imaging lens is taken into account. The power of the imaging lens determines the magnification at which the wavefront is imaged. Accordingly, the power of the imaging lenses 32, 42 is taken into account to ensure that the respective wavefronts are appropriately imaged by the science camera 34 and the imaging camera 38.

The pitch, or spacing, of the pixels to be imaged typically dictates the Nyquist frequency of the detector. Accordingly, the size and pitch of the pixels to be imaged are considered to ensure that the interferometer configuration 12 will properly resolve interference. The size of the pixel to be imaged on the science camera 34 and the imaging camera 38 is coordinated with the working f-number (also known in the art as focal ratio, f-ratio, and relative aperture) of the imaging lens 32 and the imaging lens 42, respectively. The working f-number, along with wavelength, gives the minimum feature size that can be produced by the lens under test. This is matched with the pixel size so that neither system is limiting the resolution of the other. The term "working f-number" differs from the more common term "f-number" in that the working f-number takes into account the magnification of the imaging system.

As mentioned above, the lens under test, also referred to as the test lens or optic, is immersed in a solution, such as a saline solution, within the cuvette 28. By immersing the test lens in solution, the dynamic range of the interferometer 12 is increased. This is due to the decrease in the difference in refractive index between the test optic and the surrounding medium. In terms of power, there exists an upper limit in the amount of power that can be accurately tested for any particular interferometer. This upper limit is correlated with such parameters as pixel size, pixel spacing, and imaging lens diameter. When the test optic is immersed, the power in the transmitted wavefront is reduced, thereby increasing the dynamic range of the interferometer 12. In an exemplary embodiment, a highly sensitive camera with both high pixel density and large grayscale resolution is used in conjunction with immersion to provide a test bed with an acceptable level of both sensitivity and dynamic range. Combining the sensitivity of interferometry with the increased dynamic range of immersion provides a practical technique for testing over a wide range of powers, designs, and materials.

Even with the immersion in solution, however, the base power of the test lens typically will produce interference patterns with a large number of fringes because the reference wavefront is planar. To record the high frequency fringes, in an exemplary embodiment, the science camera 34 comprises a four mega pixel CCD detector, over 28 mm square. It is emphasized, however, that the implementation of a four mega pixel CCD camera is exemplary, and that any appropriate detector can be utilized. By having enough resolution to resolve the high frequency fringes, the science camera 34 provides high spatial resolution in the measurement. To facilitate such a large array, the sensor of the science camera 34 utilizes a full frame architecture. The full frame architecture incorporates an external shutter in order to properly readout the charge. In an exemplary embodiment, to provide shuttering, an acoustic-optic (AO) modulator is used in conjunction with the spatial filter used for beam cleaning. When turned on and aligned, the modulator produces a first order beam containing the majority of the incident laser light. This first order beam is aligned to the spatial filter. When the modulator is turned off, only the zero-order beam (which is blocked by the spatial filter) is present. Thus the modulator and spatial filter create an on/off switch for the light into the interferometer. The AO modulator is driven by the science camera 34; thus shuttering and readout occur concurrently.

As mentioned above, reverse raytracing facilitates the generation of theoretical wavefronts, which are used to evaluate performance at the transmitted wavefront. One way to understand how the theoretical wavefront is generated is to consider what is being detected: the interference produced by two wavefronts in the plane of the detector (e.g., science camera 34). In accordance with phase shifting interferometry (PSI), the interference reveals the relative optical path difference (OPD) between the two wavefronts. The desired wavefront, however, is the test wavefront at the test part (lens under test), and not at the science camera 34. To obtain the desired wavefront, a known reference wavefront is used in conjunction with the OPD to infer the unknown test wavefront at the science camera 34. As the test wavefront propagates through the optics of interferometer 12, aberrations are induced. A calibration process is used to convert this inferred test wavefront at the science camera 34 into a best estimate of the test wavefront at the contact lens.

A portion of the induced aberrations depend on the incident wavefront. However, the magnitude of the added aberrations is typically a small fraction of the wavefront's magnitude. This allows for the aberrations to be treated as a perturbation to the wavefront. Mathematically, the operation of imaging the wavefront is defined in this context as:

$$Img\{W\}=W+A\{W\} \quad (1)$$

where W represents the original wavefront, and $A\{W\}$ represents the induced aberrations. The notation $A\{W\}$ is used to indicate that the induced aberrations are wavefront dependent. The imaging lens 32 is the source of the induced aberrations. One way to see why different wavefronts receive different aberrations is to view the different wavefronts as shifts in conjugates. The conjugates for the interferometer's imaging lens 32 are the test plane, which is the plane immediately following the test lens located in the cuvette 28, and the science camera's detector 34. While these conjugates do not change, any change to the test lens results in a different wavefront being present in the test plane, and thus a different wavefront traveling through the imaging system completed by the imaging lens 32 and the science camera's detector 34.

The detected interference patterns represent the difference between images of two wavefronts, and not the wavefronts themselves. The $OPD_T$ (OPD of test beam) between the image of the test wavefront ($W_T$) and image of the reference wavefront ($W_R$) at the detector plane is therefore represented mathematically as:

$$OPD_T=Img\{W_T\}-Img\{W_R\}=(W_T+A\{W_T\})-(W_R+A\{W_R\}) \quad (2)$$

An inverse operation to the imaging process, reverse raytracing, can be used to determine the wavefront at the lens. When the prescription of the interferometer is known, the system that generated the aberrations is not a black box, but rather a collection of optics that can be modeled. The model is the tool that enables an inverse operation to imaging, namely reverse raytracing. With reverse raytracing, the wavefront at the test plane, typically the plane immediately following the test optic, is produced from the OPD and reference wavefront at the detector by tracing rays backwards through the system. The rays are said to be traced backwards because, whereas in the interferometer light travels from test plane to detector (science camera 34), the rays are traced from detector (science camera 34) to test plane. Using Equation (1) and Equation (2), this inverse operation is defined mathematically as:

$$\tilde{W}_T = Img^{-1}\{W_T + A\{W_T\}\} = Img^{-1}\{OPD_T + Img\{W_R\}\}. \quad (3)$$

Equation 3 illustrates one means for implementing the process of reverse raytracing. With reference to the interferometer 12, rays are traced along the reference arm 36, through the imaging optics 32 and onto the detector, science camera 34. This is the image of $W_R$ ($Img\{W_R\}$). $OPD_T$ is then added to the rays, changing both their position and angle. At this point, the image of $W_T$ can be obtained. The rays are then traced back to the test plane. At the test plane the rays are converted to a wavefront, which is $\tilde{W}_T$, the estimate of the original test wavefront $W_T$. The reason that the result of the inverse operation is labeled an estimate is that a model of the interferometer is used to provide the correction. The model and the actual interferometer can differ. Correcting or enhancing the model to better match the actual interferometer can be achieved through a process known as reverse optimization. The model is verified via the magnification of the imaging lens's conjugates. Only two distances are not known from a prescription: the distance from the top of the cuvette 28 to the imaging lens 32 and the distance from the imaging lens 32 to the detector, science camera 34. In effect, these two distances are the object and image distances for the imaging lens 32. Because the imaging lens is known, knowledge of the magnification between the conjugate planes provides enough information to uniquely determine the two distances. A paraxial raytrace is used to update the model given the most recent magnification measurement.

Figure 2:
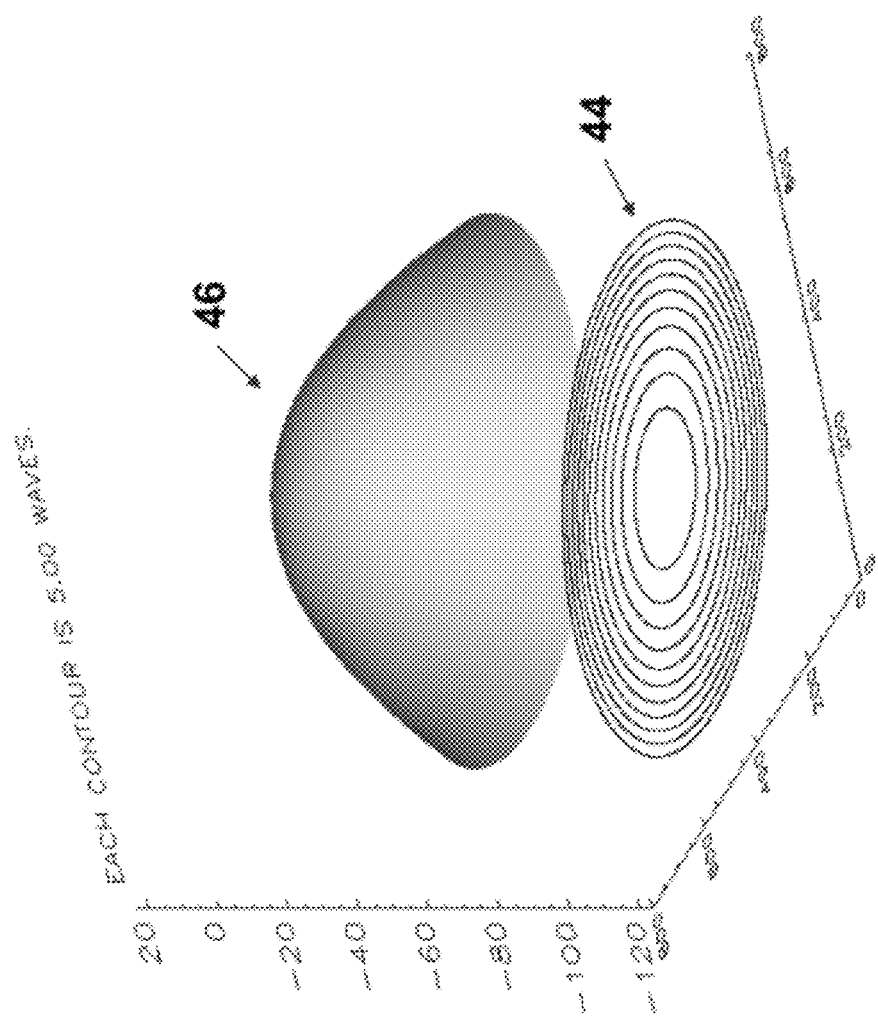
FIG. 2 depicts an image of an exemplary reference wavefront.
Figure 3:
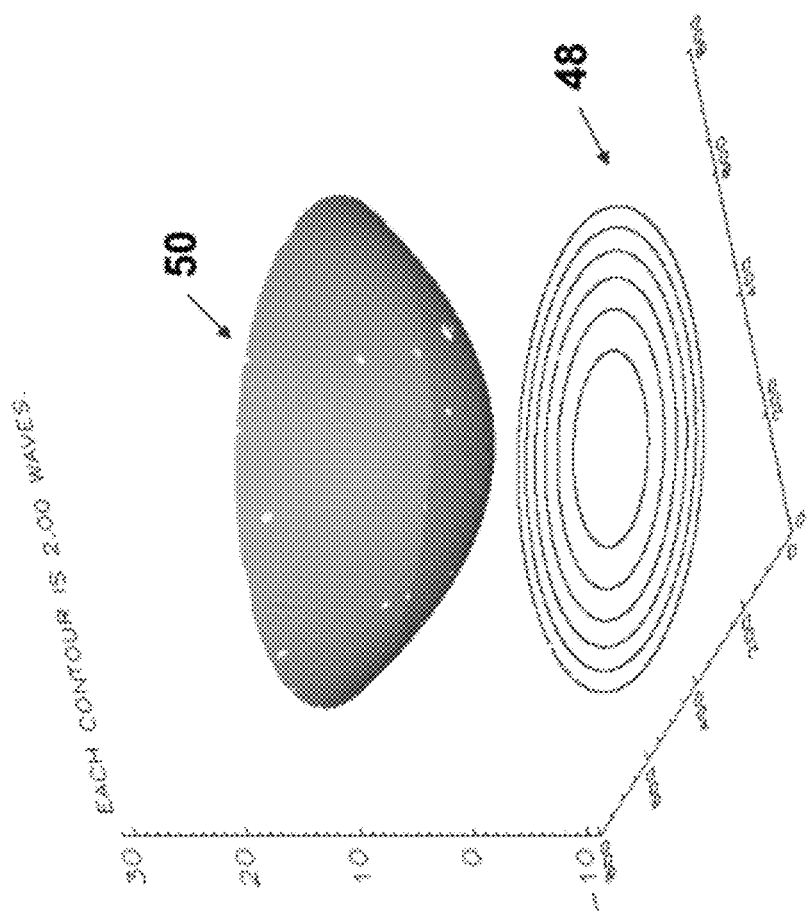
FIG. 3 depicts the transmitted optical path difference with unwanted pixels removed from a positive test lens.
Figure 4:
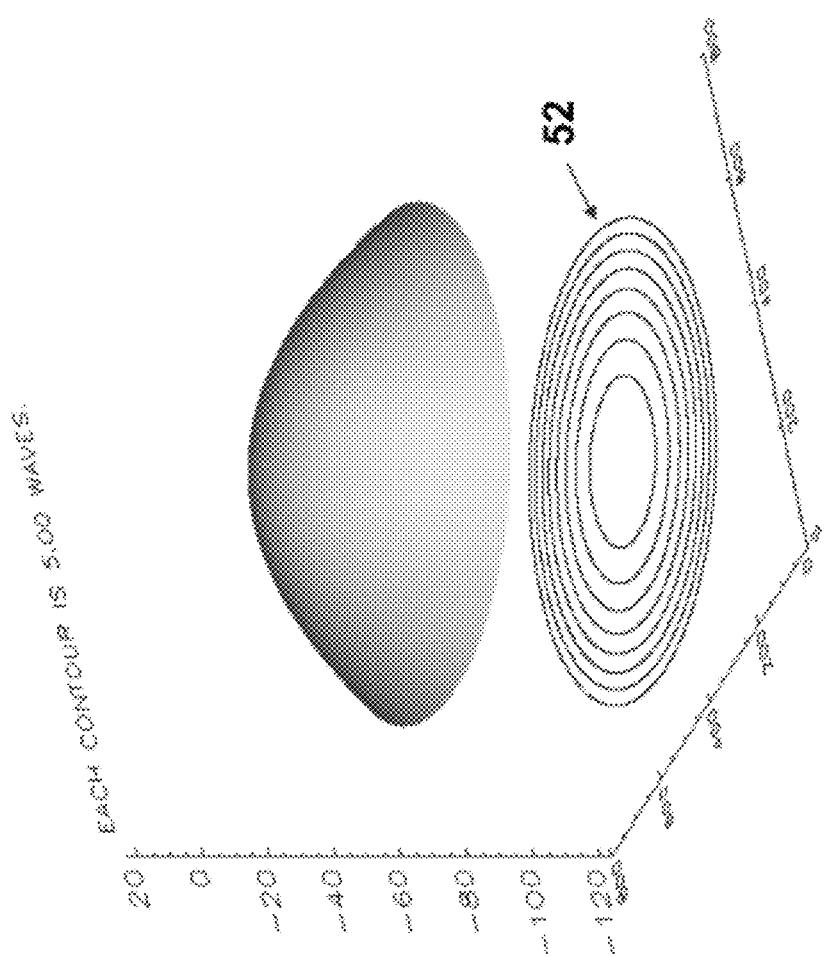
FIG. 4 depicts an exemplary image of a test wavefront.
Figure 5:
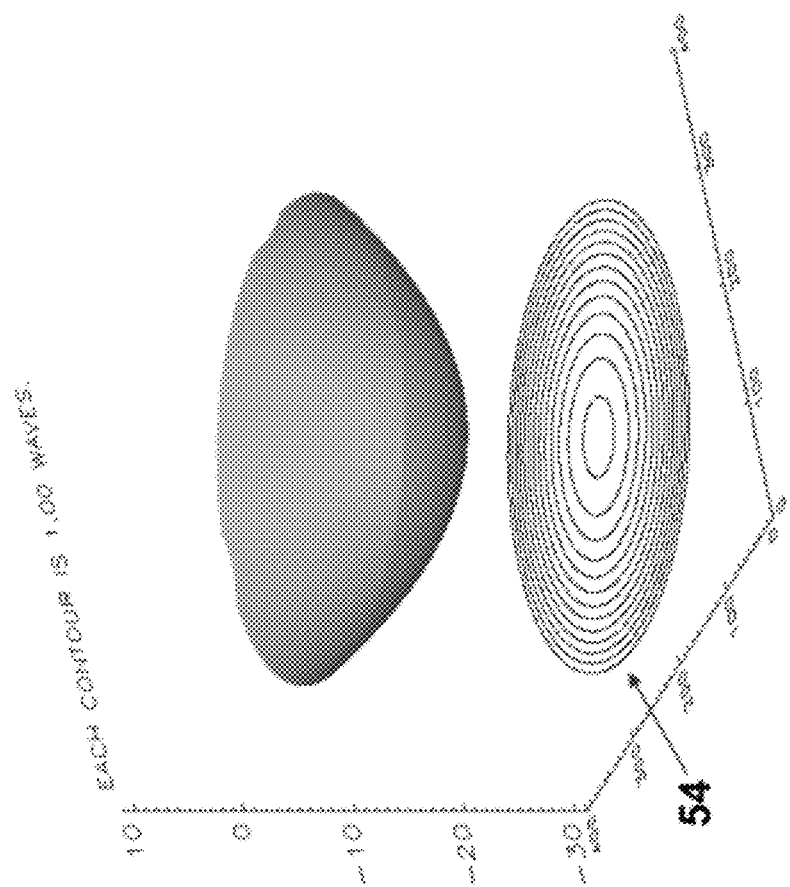
FIG. 5 depicts an estimate of a measured wavefront transmitted through a test lens.

FIG. 2, FIG. 3, FIG. 4, and FIG. 5 illustrate various wavefronts. FIG. 2 depicts an image of an exemplary reference wavefront, $W_R$ 44. The test optic 46 is a plano-convex glass lens, and the height units are waves (543.5 nm). The reference wavefront, $W_R$, 44, is shown as having a considerable amount of power, as opposed to being flat. This is because the reference wavefront, $W_R$, 44, at the detector, the science camera 34, has a considerable amount of power. As depicted in the interferometer 12 of FIG. 1, the collimated light in the reference arm 36 will produce a diverging wavefront at the science camera 34. This is an image of the reference wavefront, $W_R$, 44, because the imaging lens has as its conjugates the test plane and detector. FIG. 3 depicts $OPD_T$ 48 with unwanted pixels, representing distortion, removed from the positive test lens 50. FIG. 4 depicts an exemplary image of a test wavefront, $W_T$ 52. The measured $OPD_T$ 48 is added to the image of $W_R$ 44 to produce the image of $W_T$ 52. The images of $W_T$ 48 and $W_R$ 44 differ by $OPD_T$, the magnitude of which is considerable smaller than either wavefront. Because a positive test lens was used for this example, the image of the test wavefront has a longer radius of curvature (less sag over the aperture) than the image of the reference wavefront. Reverse raytracing is applied to the image of the test wavefront $W_T$ 52, resulting in the estimate of the measured wavefront transmitted through the test lens $\tilde{W}_T$ 54 as depicted in FIG. 5.

Figure 6:
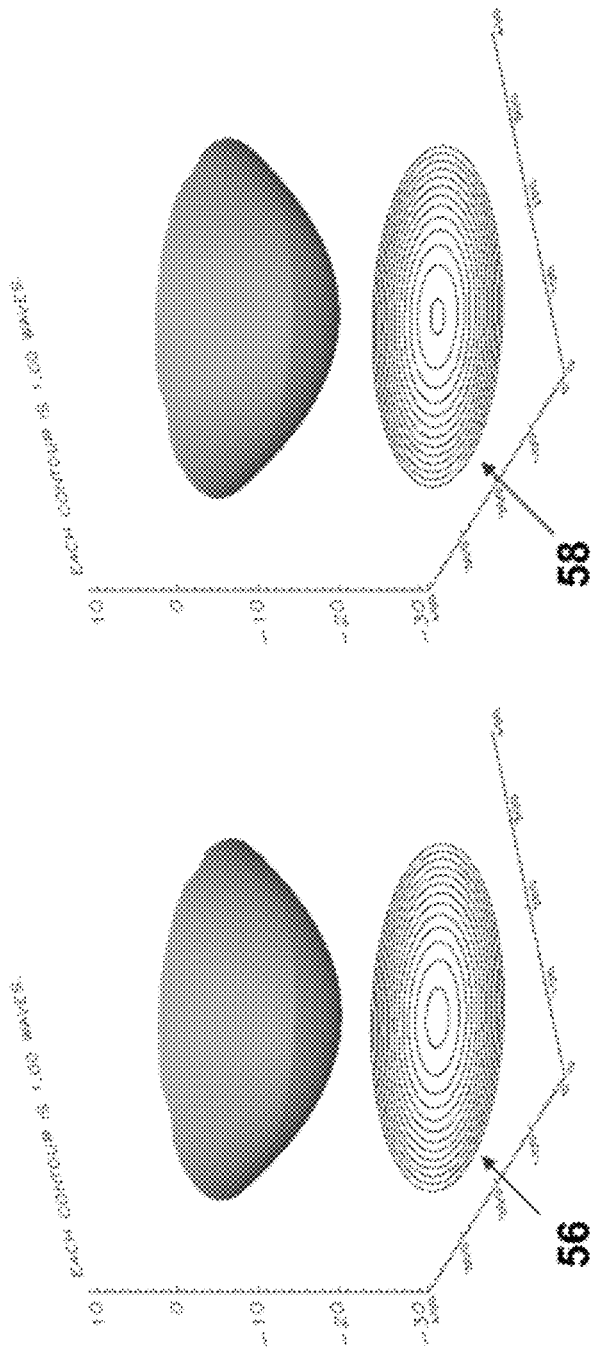
FIG. 6 shows a measured wavefront and a modeled wavefront for a calibration lens.

Utilizing the interferometer 12 and wavefront determination with reverse raytracing, comparisons can be made between a test lens and a model lens. FIG. 6 shows a measured wavefront 56 and a modeled wavefront 58 for the calibration lens. Comparisons can be made between the measured and the modeled wavefronts, providing a means for part verification, for example. To establish a comparison between measured data and modeled data, a calibration part is used. In an exemplary embodiment, a plano-convex glass lens is used as a calibration part. Parameters such as index, center thickness, and radius of curvature are measured independently, providing a complete prescription for the lens. Along with the prescription of the test part, the prescription of the interferometer enables the generation of a modeled wavefront at the same location as the measured wavefront. With two wavefronts at the same location, and therefore at the same size, a difference wavefront can be computed by simply subtracting the modeled wavefront from the measured.

Figure 7:
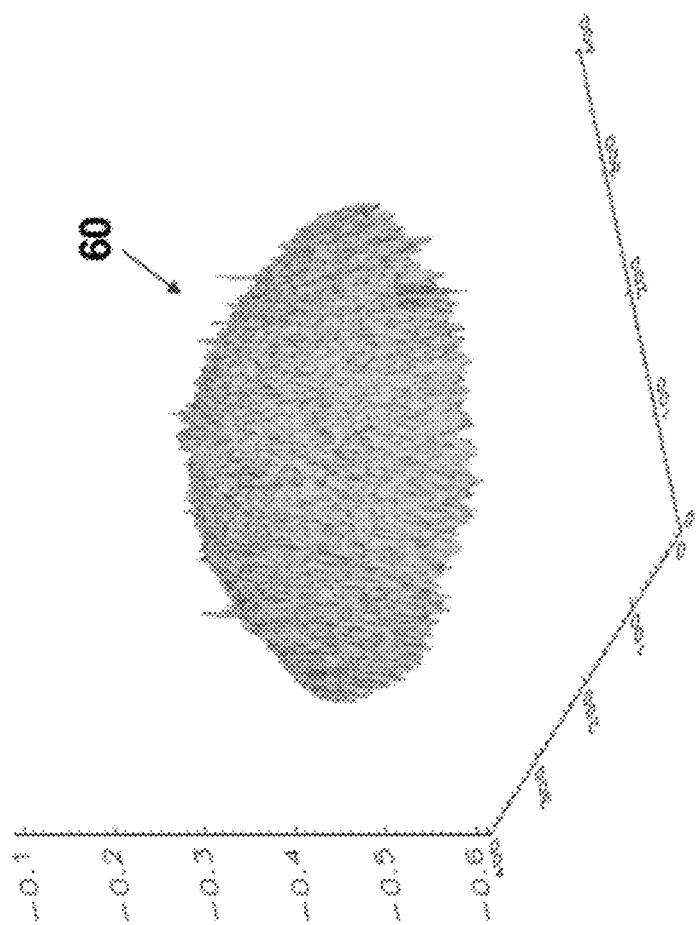
FIG. 7 depicts a difference wavefront of the difference between the measured wavefront and the modeled wavefront.

FIG. 7 depicts a difference wavefront 60 of the difference between the measured wavefront 56 and the modeled wavefront 58. This difference is computed at 99% of the diameter of the two wavefronts to avoid edge effects. The noise in the difference wavefront 60, due to a combination of factors, obscures the general shape of the difference wavefront 60. The noise in the difference wavefront 60 can be alleviated in any appropriate manner. For example, a Zernike polynomial can be applied to the difference wavefront 60 to remove the noise. Zernike polynomials are known in the art. Application of Zernike polynomials is known to cancel distortion. In an exemplary embodiment, a Zernike fitting is used to remove high spatial frequency noise, and the Zernike coefficients are used to compute aberration information about the wavefront.

Figure 8:
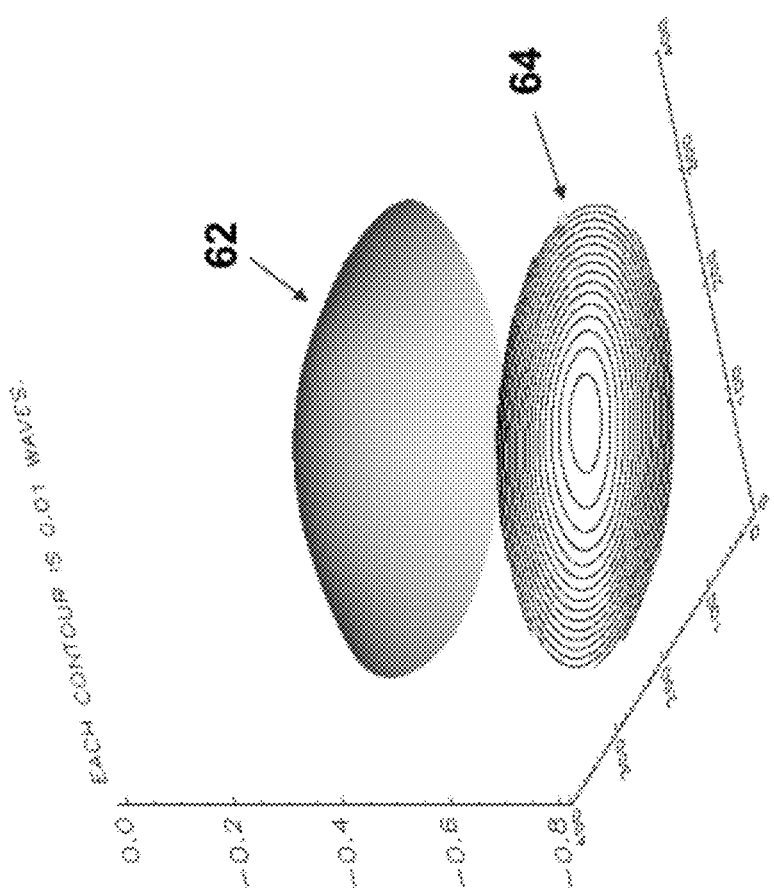
FIG. 8 shows a Zernike surface and image thereof.

FIG. 8 show a Zernike surface 62 and image 64 thereof, after application of 36-term Zernike polynomials fit to the difference wavefront 60. The Zernike surface 62 illustrates that defocus is the dominant error in the comparison between measured and modeled wavefronts. Not to be tied to a particular theory, it is presumed that a difference in power like this is most likely due to a discrepancy in index of refraction for the test lens and the surrounding saline solution in the interferometer versus the values used in the model. Using the Zernike coefficients for this difference, the power is measured at −0.019 diopters. In air, this difference becomes −0.054 diopters. Using a thin lens model, this difference in power can be converted to an uncertainty in index. The difference of −0.054 diopters, along with the prescription of the lens, gives an uncertainty for the difference in index of 0.0015. Since both index values are currently known to an uncertainty of about 0.001, the notion that the power error can be attributed to the discrepancy in index is plausible.

Figure 9:
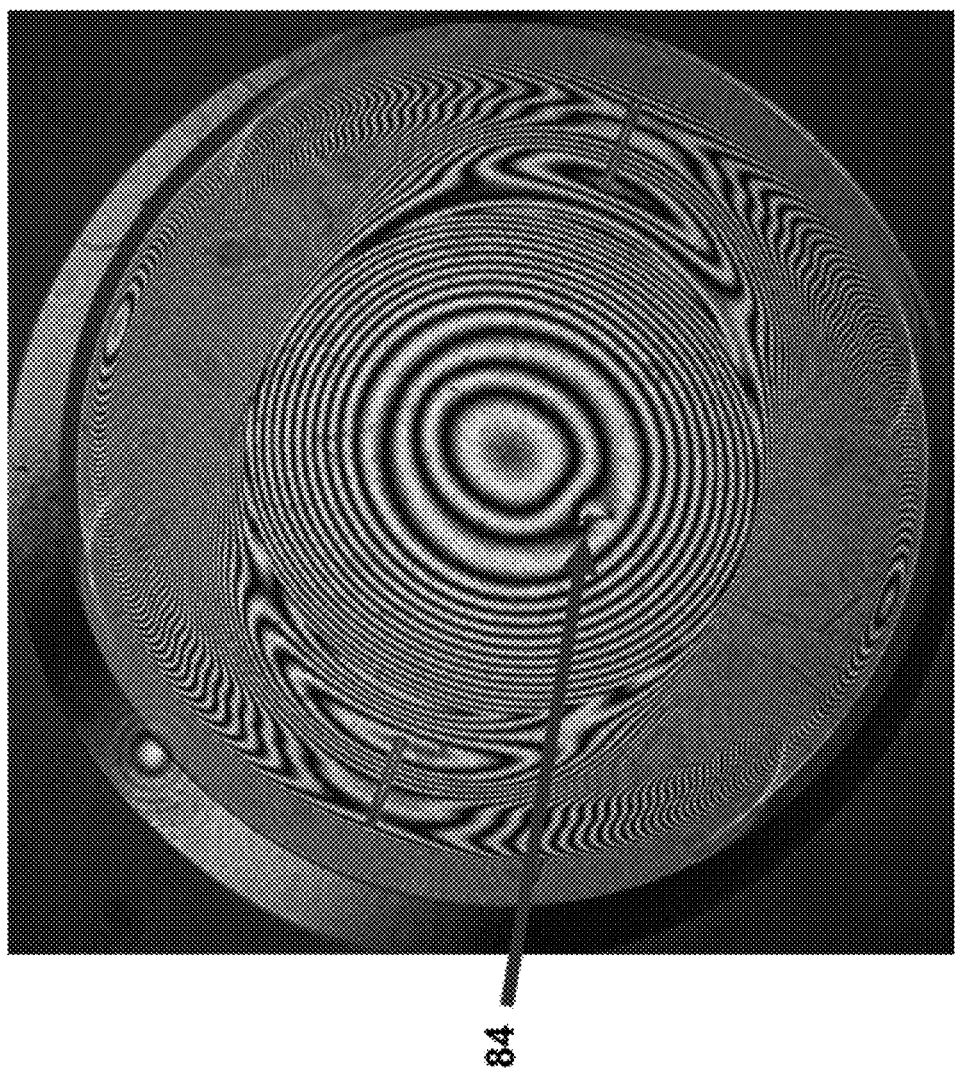
FIG. 9 shows a localized defect of a tested lens.
Figure 10:
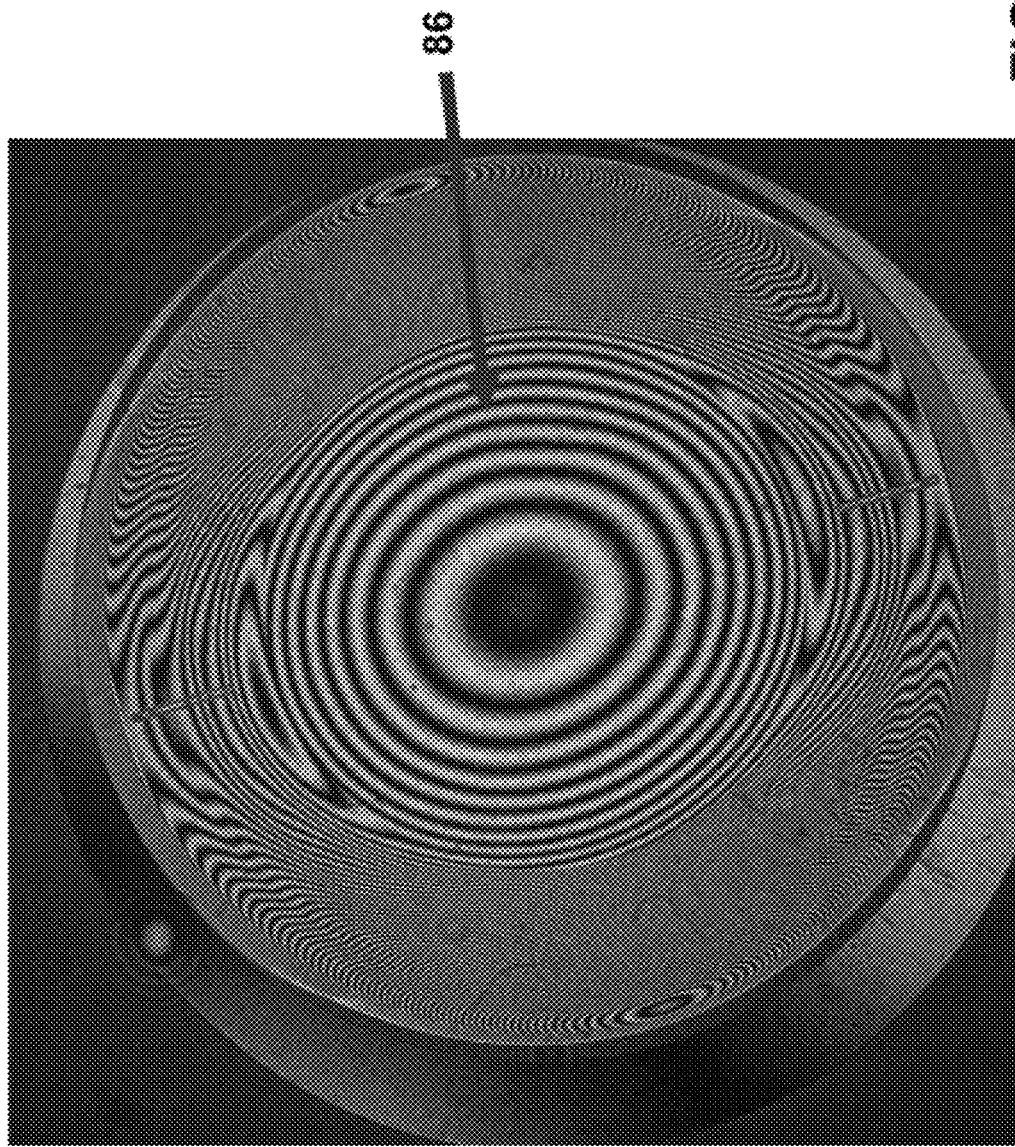
FIG. 10 shows a region in which fringes are slightly flattened.
Figure 11:
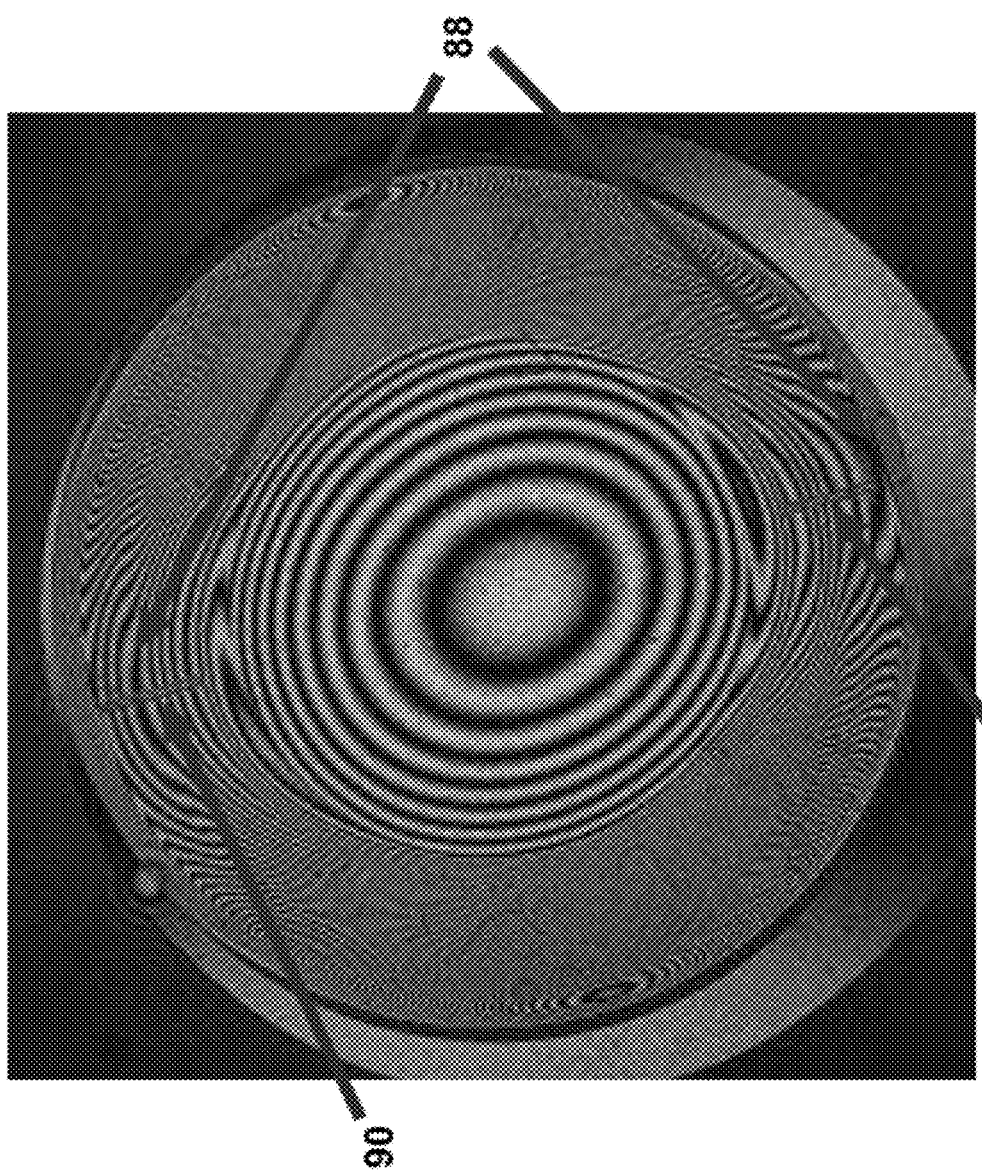
FIG. 11 shows defects indicative of possible stress or other alterations in the periphery of the lens.

In addition to testing for the ophthalmic prescription of a lens, various other characteristics and features of a lens are detectable. For example, interferogram of FIG. 9 shows a localized defect 84 of a lens under test. Thus, transmitted wavefront determination utilizing the interferometer 12 provides ability to detect defects in optical performance that cause deviations in the light path on the order of a fraction of the wavelength of light used. Further, transmitted wavefront determination utilizing the interferometer 12 can produce the spherical power of any spherical contact lens. For toric lenses, cylindrical power and axis can also be obtained. Yet further, regions that deviate from other parts of a lens are detectable, as shown in FIG. 10. FIG. 10 shows a region 86 in which the fringes are slightly flattened. The region 68 may not be characterized as a defect (e.g., defect 84 of FIG. 9), but will produce a different optical effect such as power change, spherical aberration, or the like. Transmitted wavefront determination utilizing the interferometer 12 also can detect information on possible stress or other alterations in the periphery of the lens, as shown in regions 88 of FIG. 11. Ideally, outside the optical zone, there should be symmetry in the fringe pattern about the line through the fiducial marks 90. The swirl or misalignment in the fringes 88 near the two fiducial marks 90 indicates an area of possible stress and/or misalignment.

Figure 12:
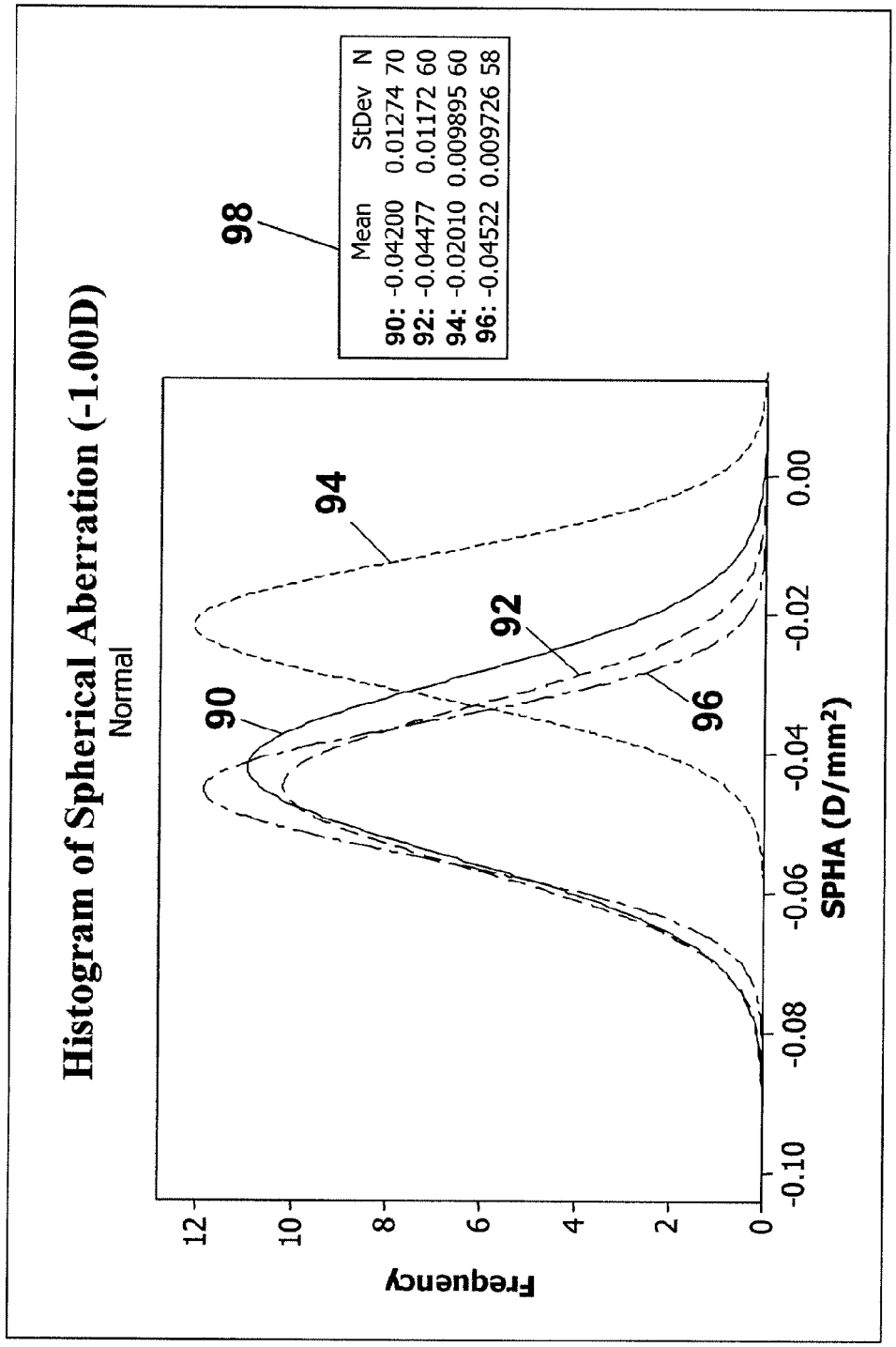
FIG. 12 shows plots of spherical aberration versus frequency for four different lenses.

A wealth of information can be produced by analyzing the transmitted wavefronts collected via the interferometer 12. This information can be used to discriminate between materials with different levels of additives, designs with different amounts of aberrations, and lenses made with the same design but different materials. For example, FIG. 12 shows plots 90, 92, 94, and 96 of spherical aberration (SPHA) in diopters per square millimeter (D/mm$^2$) versus frequency for four different lenses. Each lens tested had a power of −1.00 diopters (D). Further, statistical analysis of information obtained via wavefront analysis can be conducted as illustrated by statistic block 82, wherein the mean and standard deviation of the spherical aberration for each lens 90, 92, 94, and 96 are depicted.

Figure 13:
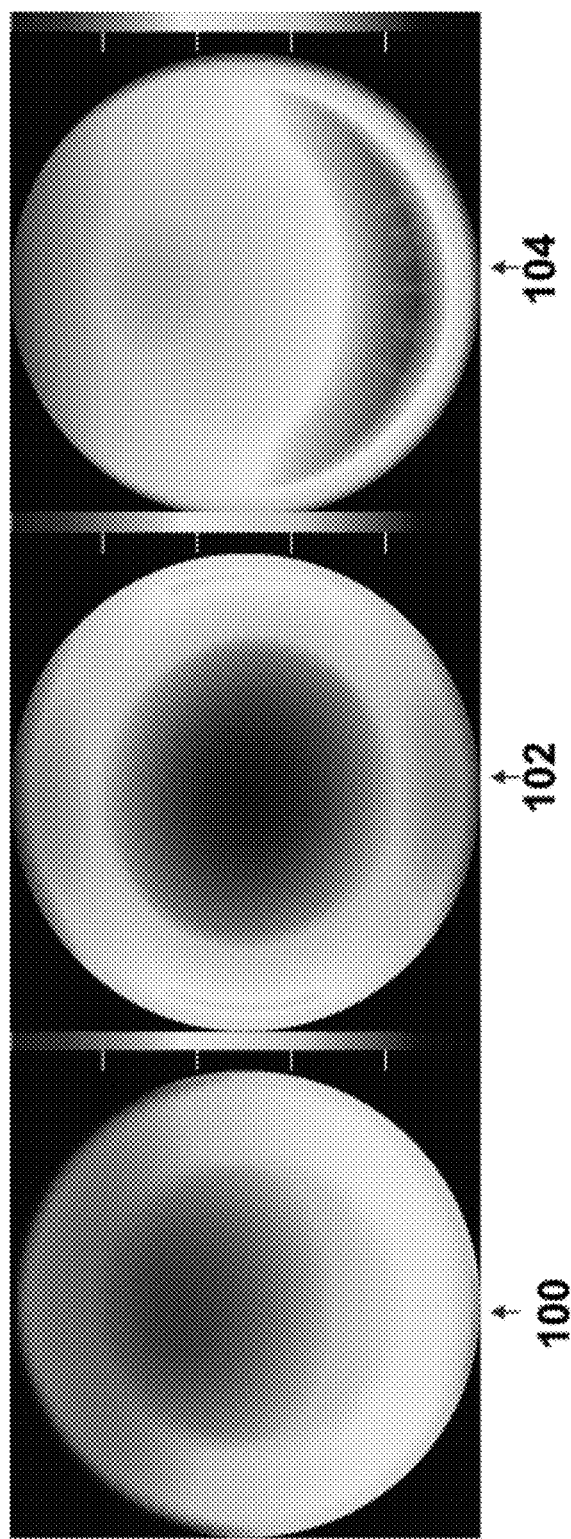
FIG. 13 shows the thickness of toric lenses.

Numerous other lens characteristics and parameters can be obtained via wavefront analysis. For example, the thickness of toric lenses can be determined as illustrated in FIG. 13. Toric contact lenses are spherocylinder lenses designed to correct astigmatism in the eye. In FIG. 13, the thicknesses of three lenses 100, 102, and 104 is depicted. The darker areas indicate increased thickness compared to lighter areas for each lens, having a range from 0.0 mm to 0.500 mm.

Figure 14:
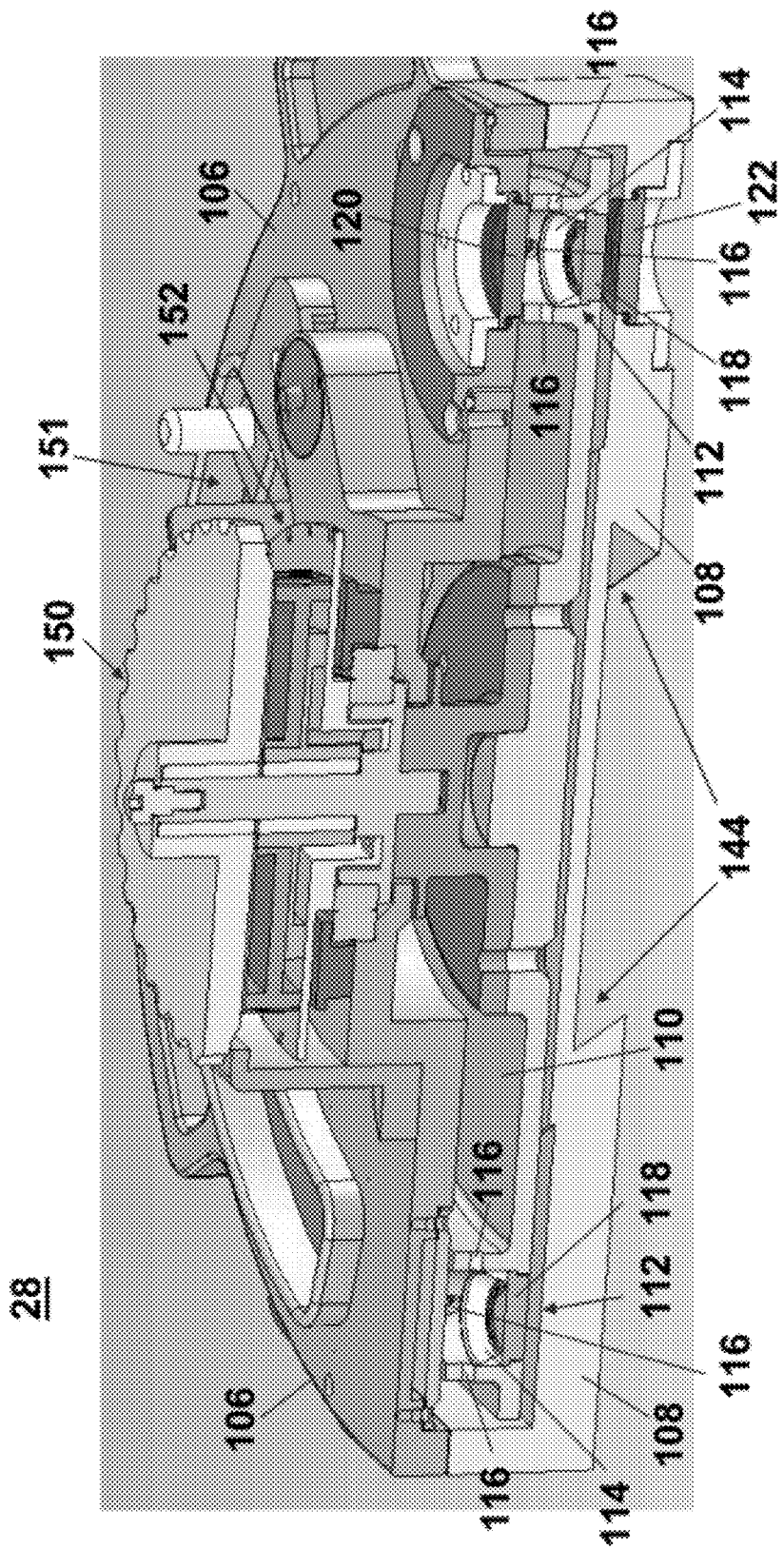
FIG. 14 is a cross-sectional view of the cuvette.

As described above, lenses under test can be placed in a cuvette in which they are submerged in a solution (e.g., saline solution). FIG. 14 is a cross-sectional view of the cuvette 28 shown in the interferometer 12 depicted in FIG. 1. Utilizing the cuvette 28, lenses remain in solution during testing. Materials used in manufacturing contact lenses include hydrogels, which are hygroscopic. The lenses are placed in the cuvette 28, or water cell, to keeps them hydrated and stable in terms of refractive index. The cuvette 28 comprises a compartment having two windows that are antireflection (AR) coated. The lens under test is positioned between the two windows. The windows are AR coated on their external surfaces. The index match between the window glass and solution eliminates the need for an AR coating on the internal surfaces.

Generally, and as described in more detail below, the entire cuvette interfaces with a test configuration, such as the interferometer 12 for example, via a kinematic mount and by means of an automatic connection system that includes the mechanical linkage to the interferometer drive system and the electrical control and instrumentation circuits. An outer enclosure houses all the constituents of the cuvette. The enclosure is configured to evenly circulate the test solution, to prevent the test solution from leaking, and to monitor the temperature of the test solution. A lens holder contains one, or multiple, testing cells, configured to hold a lens submerged in a solution, and which can be moved within the cuvette's outer enclosure while maintaining the placement and orientation of the test lenses. A first window is configured to allow the interferometer test arm beam to enter a cell with no change in collimation or in coherence length. A second window is configured to allow the test arm beam to exit the cuvette after passing through the lens with no additional change to the exiting test arm beam. The centers of the two optical windows are aligned with each other, with the movable lens holder mounted between. The holder is moved so as to position each cell, one at a time, between the first window and the second window.

The cuvette kinematic mount is achieved by use of a dovetail slide, which provides the primary alignment of the cuvette to the mechanical and electrical connectors and sensors and provides vertical height registration use of locator pins and a resilient (e.g., spring-loaded) arm, which provides a radial force against the locator pins, to accurately and consistently locate the cuvette in a plane parallel to the dovetail slide. The mechanical linkage is designed to provide repeatable, positive engagement and vibration isolation between the cuvette and the interferometer without any preconditioning to the cuvette's linkage.

Each cell in the lens holder has a window that does not change the collimation or coherence length of an incident collimated beam, and which is transparent to the wavelength or wavelengths of the interferometer's coherent light source. This window forms the surface on which the test lens is mounted. The window in each cell in the lens holder is coplanar with all other cell windows in the lens holder. Each cell in the lens holder has a tapered wall designed to allow for accurate and distortion-free mounting of the test lens in the cell. Each cell is designed so that the interferometer's imaging camera can image the entire lens. Each cell in the lens holder has at least one channel to allow solution to flow. Both optical windows in the cuvette are transparent to the wavelength or wavelengths of the interferometer's coherent light source. The test solution circulating through the cuvette is optically transparent to the wavelength or wavelengths of the interferometer's coherent light source. Example test solutions include saline solutions, buffered saline solution, deionized water, solutions with active pharmaceuticals, or a combination thereof.

The outer enclosure of the cuvette includes inlet and outlet connections for a source of temperature controlled test solution. The outer enclosure is configured to monitor the temperature of the test solution using a temperature probe. In an example configuration, the temperature probe comprises a resistance temperature detector (RTD) that provides information to an external temperature controller to help stabilize the temperature of the solution in the cuvette. In an example configuration, the outer enclosure of the cuvette is constructed from an opaque polycarbonate material that is mechanically stable in the presence of the test solutions.

The cuvette is configured to handle a variety of types of lenses, such as hard contact lenses, hard refractive contact lenses, hard diffractive contact lenses, hard hybrid refractive/diffractive contact lenses, soft contact lenses, soft refractive contact lenses, soft diffractive contact lenses, soft hybrid refractive/diffractive contact lenses, hard contact lenses comprising an active pharmaceutical, soft contact lenses comprising an active pharmaceutical, single vision lenses, toric lenses, bifocal contact lenses, multifocal lenses, cosmetically tinted lenses, freeform lenses, an intraocular lenses, an intraocular refractive lenses, an intraocular diffractive lenses, intraocular hybrid refractive/diffractive lenses, accommodating lenses, spectacle lenses, refractive spectacle lenses, diffractive spectacle lenses, and hybrid refractive/diffractive spectacle lenses, for example.

Referring to FIG. 14, the cuvette 28 is a vessel for holding contact lenses immersed in solution in such a way that the lenses can be tested using the interferometer 12. The cuvette 28 is designed to accommodate multiple lenses. In an exemplary embodiment, the cuvette 28 can hold 30 lenses. Each lens has its own location (cell) in the cuvette 28, and the cells are mobile within the cuvette 28. Lenses can be positioned for testing within the cuvette 28, and preferably are not deformed by the cuvette or any internal mounting within it. It is also preferably that the entire lens under test be visible. All windows of the cuvette preferably are of equal optical quality in terms of flatness to prevent adding additional power to the transmitted wavefront. The location and presentation of the lens preferably is repeatable lens-to-lens and trial-to-trial. Insertion and removal of lenses into and from the cuvette 28 typically is simple and straightforward. Lenses preferably are not free to move outside their cells, and bubbles formed in the solution should not interfere with measurements. That is, the bubbles should not be visible in a cell.

The cuvette 28 comprises outer walls 106 and 108. The portion 110, or carousel, in the middle of the cuvette 28, comprises multiple lens cells 112. In an exemplary embodiment, the carousel 110 comprises 30 lens cells 112. Each cell 112 comprises of a tapered walls 114 (which can conform to a lens), channels 116 for fluid flow, and a window 118 at the bottom of the cell on which the lens rests. The outer walls 106 and 108 can comprise any appropriate material. In an exemplary embodiment, the outer walls 106 and 108 comprise polycarbonate. Polycarbonate provides the following characteristics to the cuvette 28: lightweight, opaque, chemically inert, and low water absorption, which keeps the cuvette 28 dimensionally stable.

Figure 15:
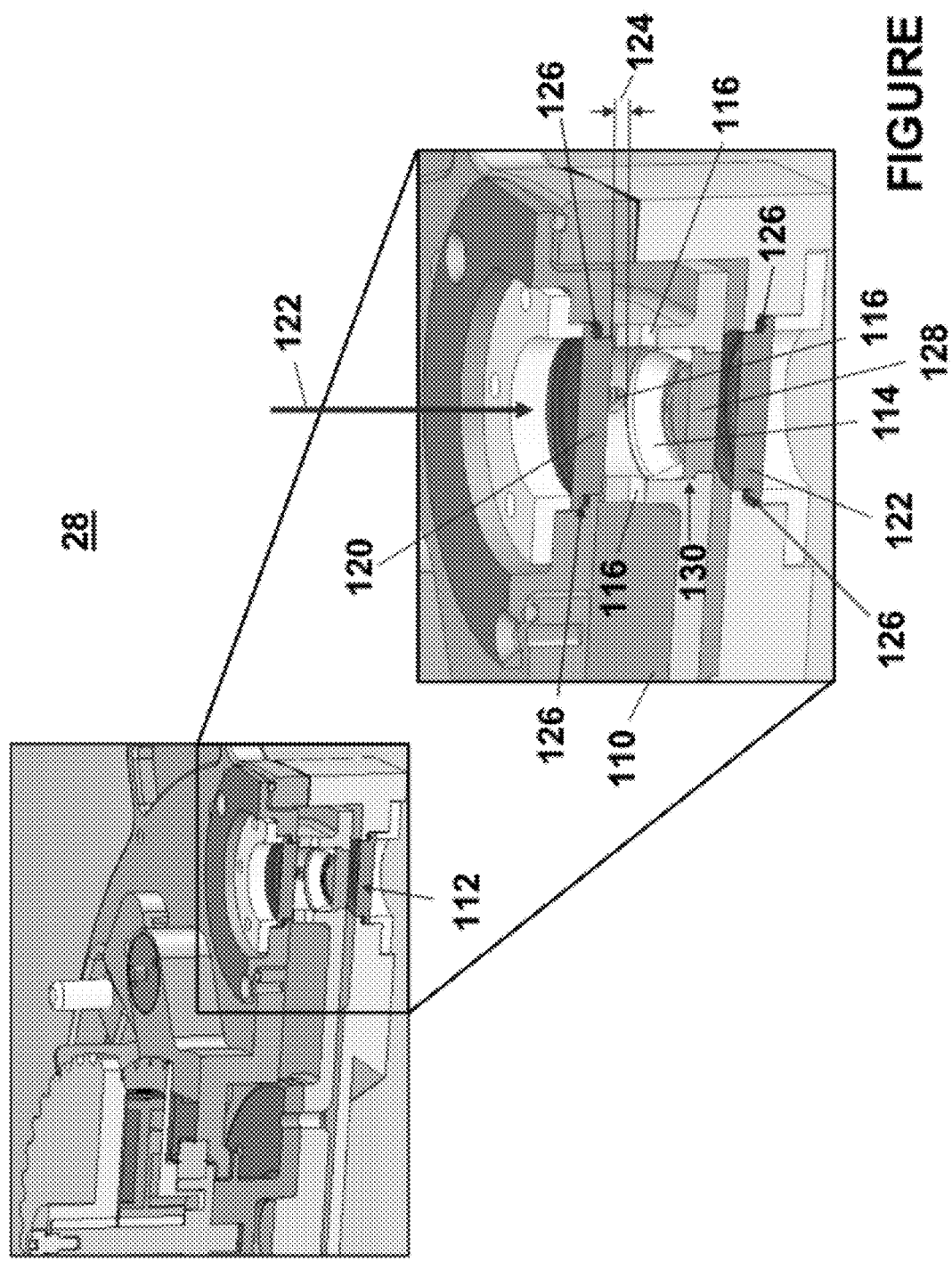
FIG. 15 is an illustration of an expanded cross-sectional view of a portion of the cuvette.

FIG. 15 is an illustration of an expanded cross-sectional view of a portion of the cuvette 28. Light from the interferometer 12 enters the cuvette 28 through the top window 120 in the direction of arrow 122, and travels down through the lens which is resting in its lens cell 112, and then exits the cuvette through the bottom window 122.

In an exemplary embodiment, there is little distance, labeled 124 in FIG. 15, between the top of the lens cell wall 114 and the top window 120. This small gap 124 is maintained throughout the cuvette 28, and is designed to keep the lenses in their respective cells 112 during rotation. Also, in an exemplary embodiment, there are four notches 116 in each lens cell 112. Notches 116 allow the circulating solution to easily flow through each cell 112, thereby keeping all the cells 112 at thermal equilibrium. It is emphasized that the number of notches 116 depicted in cuvette 28 is exemplary, and that any appropriate number of notches can be implemented. The outer windows 120 and 122 are stepped to provide a channel 126 for an O-ring or gasket to sit and provide a seal around each window 120, 122. This configuration also allows the windows to be tipped and/or tilted into alignment, rather than relying on a fixed mounting scheme. The middle glass window 128 is also stepped, see area 130, to provide consistent registration amongst all cells 112. In an exemplary embodiment, the middle window 128 protrudes from the bottom of the carousel 110 to keep bubbles in the solution away from the central portion of the window 128. The tapered sides 114 of each cell 112 ease centering of the lens, and do not deform the lens in any way. In addition, the wall sides 114 aid in unloading lenses, as lenses can be slid up the side of the cells 112 and then removed from the cuvette 28 once outside the cell 112. Loading and unloading of lenses can be accomplished through a door 151, or the like, of the cuvette 28. In an exemplary configuration, the door is attached to an interlock (see interlock 188 in FIG. 19) that prevents automatic carousel rotation when the door is open. No special tool is required to work with the lenses, for example a swab can be used to work with the lenses.

In order make measurements on multiple lenses with the interferometer 12 with no user requirements, in an exemplary embodiment the interferometer 12 controls the cuvette 28 via automatic indexing. Automatic indexing can be accomplished via any appropriate means. For example, the cuvette 28 can have its own motor and processor, and simply receive signals from the interferometer 12. In another example embodiment, more control is contained in the interferometer 12, and less control contained in the cuvette 28. In this embodiment, the interferometer 12 provides a means for rotation that mates with the cuvette 28. This can be accomplished, for example, by use of a gear, belt, chain, rack and pinion or the like, or a combination thereof.

Figure 16:
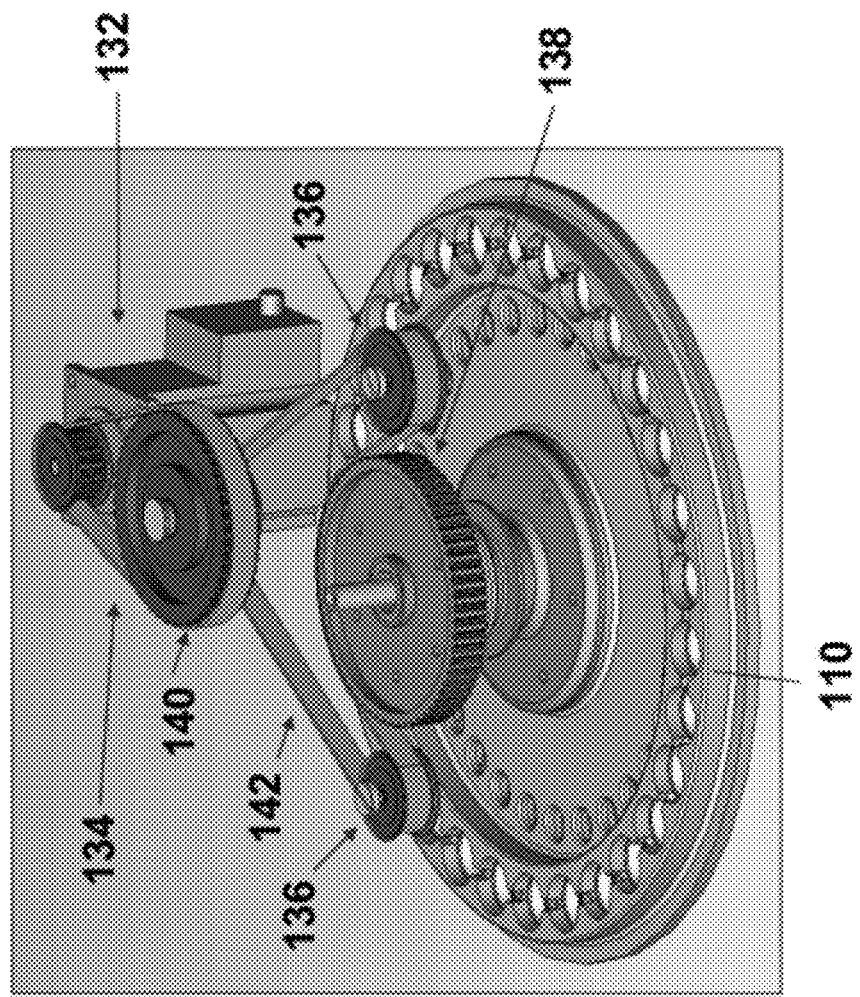
FIG. 16 depicts an exemplary coupling mechanism.

FIG. 16 depicts an exemplary coupling mechanism that comprises a single motor 132, a gear box 134, pulleys 136, 138, 140, and a grooved belt 142. The carousel 110 up through the cuvette pulley 138 are contained within the cuvette 28. The motor 132, gear box 134, drive pulley 140, and tensioner pulleys 136 are fixed components within the interferometer 12. Coupling occurs between the cuvette pulley 138 and geared belt 142 when the cuvette 28 is pushed into the interferometer 12. This type of coupling provides significant engagement around the pulley, reducing the possibility of slippage. The large amount of engagement eases starting and stopping cuvette rotation. The stresses in this system are low, and the flexibility of the belt mitigates any coupling between the motor and cuvette. Also, the flexibility of the belt dampens any backlash introduced by the motor 132. This design keeps carousel 110 suspended; no part of the carousel 110 rides along the bottom of the cuvette 28. This eliminates friction and stiction (static friction), and thereby improves positional accuracy.

No set rotation point typically is required for loading; the belt 142 and pulley 138 will mate regardless. The tensioner pulleys 136 can be adjusted as needed to keep the loading forces consistent. The robustness of a belt system is favorable for use with multiple cuvettes 28. To load a cuvette 28 into the interferometer 12, the cuvette 28 is simply pushed-in/pulled-out the along a dovetail 144 (see FIG. 14) of the cuvette 28. The dovetail 144 provides vertical stability when the cuvette 28 is mated with the interferometer 12 and positional sensors that control automatic indexing.

Figure 17:
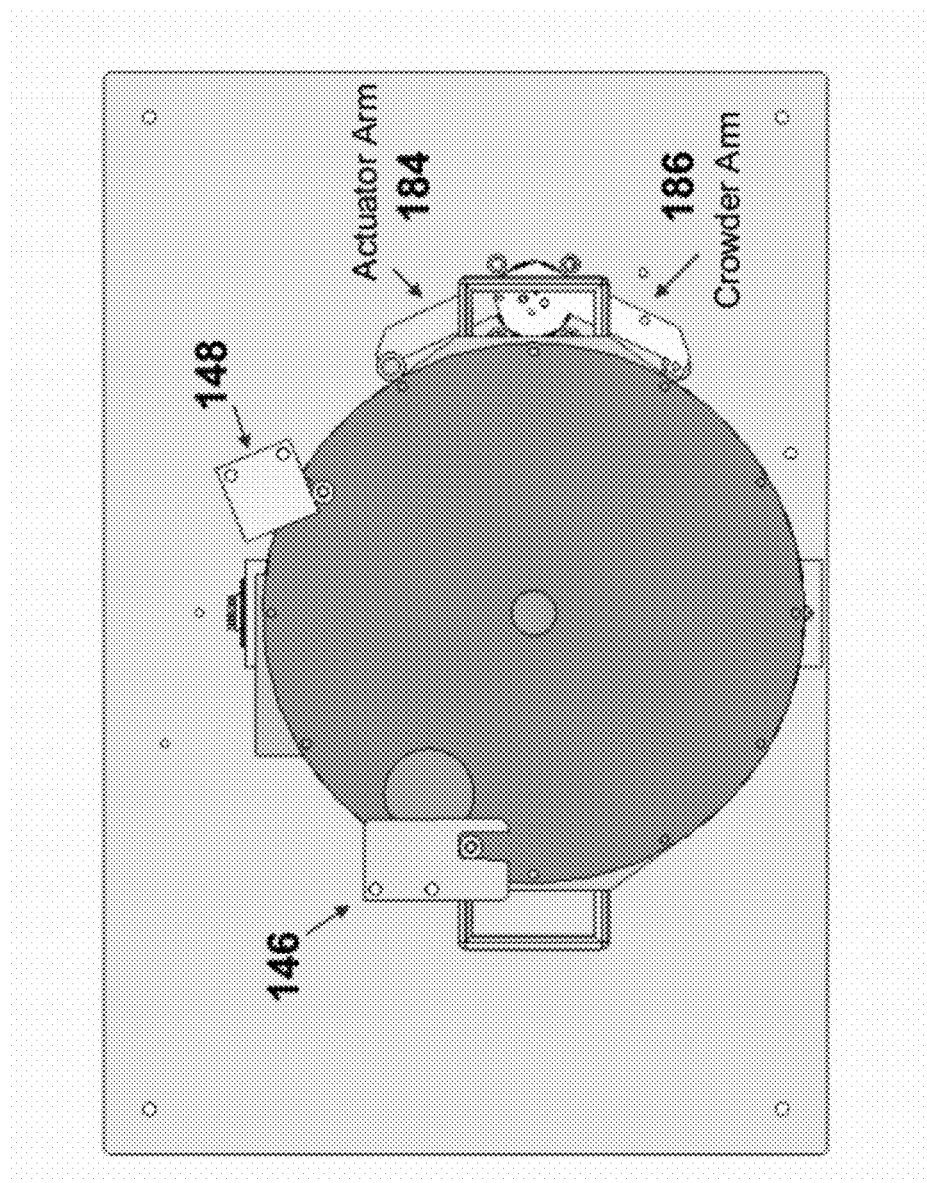
FIG. 17 is a top view of an illustration of a cuvette positioning mechanism.

FIG. 17 is a top view of an illustration of a cuvette positioning mechanism. In an exemplary embodiment, the location of a cell 112 is determined by two locator pins which are part of XY locator 146 and radial location 148, respectively. Combined with a loose-fitting dovetail 144, the two locator pins provide repeatable, kinematical positioning of the cuvette. The designed coupling allows for manual rotation. The sprocket 150 (see FIG. 14) provides manual rotation and is clutched for safety purposes; a pinch point is avoided between the sprocket and interferometer when the cuvette is loaded into the system. The actuator arm 184 and crowder arm 186 work as pair to provide a spring loaded force which keeps the cuvette 28 pressed against the XY locator 146 and the radial locator 148 via a radial force. Thus the two arms 184 and 186 enable kinematic loading of the cuvette 28 to the interferometer.

Figure 18:
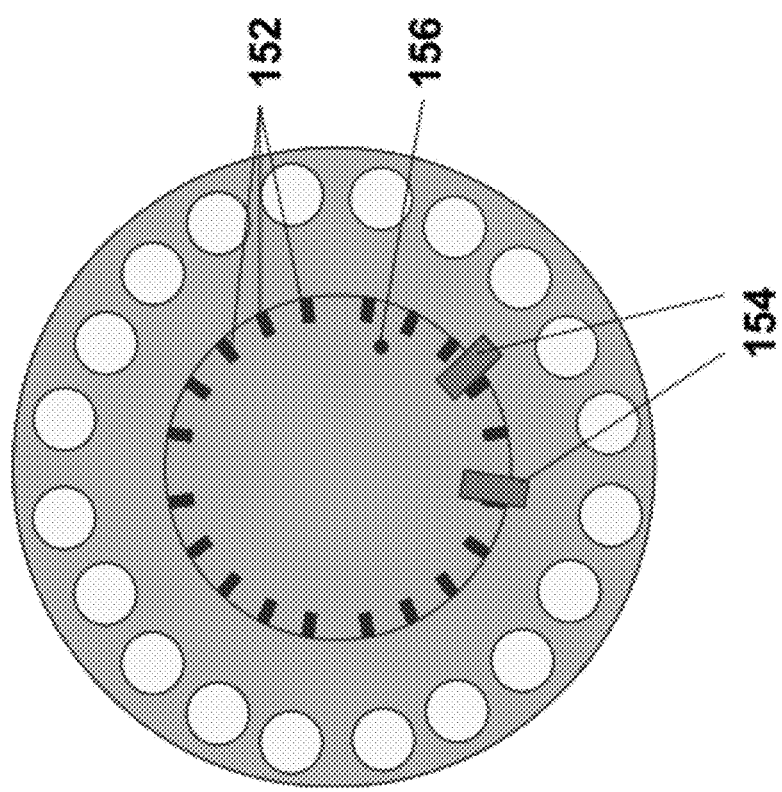
FIG. 18 is an illustration of positional flags and positional sensors.

Automatic indexing is provided by the wheel with flags 152 (see FIG. 14) located just below the sprocket 150. The flags 152 interface with positional sensors 154 attached to the interferometer 12, as shown in FIG. 18. As the cuvette 28 rotates, the flags 152 trigger the positional sensors 154, which then send commands to slow and then stop the cuvette 28. Only three cell position sensors 152 are labeled in FIG. 18 for the sake of simplicity. The cuvette 28 is slowed to minimize disturbing the loaded lenses. Lens positioning is independent of the mechanism used to rotate the cuvette 28. The motors simply start and stop based off signals from the positional sensors 154. No counts or other motor settings are used to determine cell positions. Home position flag 156 is used to initialize alignment of the cuvette 28 with the interferometer 12.

FIG. 19 is a diagram of an enclosed cuvette 28. The enclosed cuvette 28 provides temperature stability by circulating solution between the cuvette 28 and an external chiller (external chiller not shown in FIG. 19). The design of the cuvette's interior allows fluid to flow through and between cells 112. The cuvette comprises three elements for fluid control: a temperature probe 158, an intake valve 160, and a drain 162. In addition, an overflow coupling 164 is also provided. The temperature probe 158 provides an electronic reading of the temperature of the fluid inside the cuvette 28 near the measurement windows. The intake valve 160 and drain 162 provide ports for solution to circulate through the cuvette 28. The intake portion allows solution to enter the cuvette 28 and the drain portion allows solution to exit the cuvette 28. The intake valve 160 and drain 162 interface with the external chiller and pump through tubes equipped with the appropriate fittings.

An interferometer 12 with cuvette 28 provides a viable method and system for utilizing wavefront analysis to test contact lenses. Testing against a planar reference wavefront enables the determination of the absolute lens power. The increase in dynamic range due to the immersion of the lenses in saline solution allows for a wide range of prescriptions to be tested without the use of null optics or other means of removing the bulk power of the lens. This method and system is applicable to a wide variety of lenses, including spherical lenses. No assumption is necessary regarding the type of part being tested. All that is needed is the prescription of the test lens.

FIG. 20 is a flow diagram of an example process for aligning detectors of an interferometer configuration for obtaining a wavefront of a lens. In an exemplary embodiment, the cameras (e.g., the imaging camera 38 and the science camera 34) are aligned prior to testing a lens. Alignment comprises converting the imaging camera's 38 coordinate system to the science camera's 34 coordinate system. To accomplish alignment, an image point in the imaging camera's 38 is selected and a corresponding image point is determined in the science camera 34. The image camera 38 and the science camera 34 differ, at least, in magnification capability. Also, the cameras can differ in respective shift in x-axis, y-axis, and/or rotation of corresponding image points.

In an example alignment process, a test target (e.g., a target lens having known reference points) is utilized to determine the relationship between the two cameras. FIG. 21 shows an example target lens 178. The target lens 178 comprises ten concentric circles. Example image point 180 has a location of 0 on the x-axis and 1 on the y-axis. This is denoted as (0,1) in FIG. 21. Example image point 182 has a location of −2 on the x-axis and 0 on the y-axis. This is denoted as (−2,0) in FIG. 21. To calibrate the detectors, points of intersections with the x and y axes and the circles are utilized. Using the test target, in an example process, five values are determined. At step 166, the magnification of the first detector (e.g., the science camera 34) is determined. The magnification of the science camera is referred to herein as $m_S$. The magnification of the second detector (e.g., the imaging camera 38) is determined at step 168. The magnification of the imaging camera is referred to herein as $m_I$. At step 170, the location on the x-axis of the science camera 34 corresponding to the location of the x-axis location zero on the imaging camera 38 is determined. This location on the x-axis of the science camera 34 is referred to herein as $x_0$. At step 172, the location on the y-axis of the science camera 34 corresponding to the location of the y-axis location zero on the imaging camera 38 is determined. This location on the y-axis of the science camera 34 is referred to herein as $y_0$. The angle of rotational difference between the science camera 34 and the imaging camera 38 is determined at step 174. This angle of rotational difference is referred to herein as $\theta_S$. At step 176, using the determined values of $m_I$, $m_S$, $x_0$, $y_0$, and $\theta_S$ the location of the center of the target lens measured in the imaging camera 38 is converted to the corresponding location in the science camera 34. More generally, the values of $m_I$, $m_S$, $x_0$, $y_0$, and $\theta_S$ are utilized to convert the imaging camera's 38 coordinate system to the science camera's 34 coordinate system.

In an example embodiment, the coordinates in the coordinate system of the science camera 34 are converted from the coordinates in the coordinate system of the science camera for a corresponding point in accordance with the following formulas.

$$x_s = (x_1 * \cos\theta_s + y_1 * \sin\theta_s) m_I / m_S + x_0 \quad (4)$$

$$y_s = (-x_1 * \sin\theta_S + y_1 * \cos\theta_S) m_I / m_S + y_0, \quad (5)$$

where: $x_S$ represents an x-axis location in the science camera corresponding to the x-axis location of the corresponding point in the imaging camera, $y_S$ represents the y-axis location in the science camera corresponding to the y-axis location of the corresponding point in the imaging camera, $m_S$ represents the magnification of the science camera 34, $m_I$ represents the magnification of the imaging camera 38, $x_0$ represents the location on the x-axis of the science camera 34 of the x-axis location zero in the imaging camera 38, $y_0$ represents the location on the y-axis of the science camera 34 of the y-axis location zero in the imaging camera 38, and $\theta_S$ represents the angle of rotational difference between the science camera 38 and the imaging camera 34.

In an example embodiment, the interferograms obtained from the science camera and the imaging camera are combined into a single wavefront for a portion of the lens under test. The interference patterns at both the science camera and the imaging camera are captured. The modulation is computed for the imaging camera. Computing the modulation results in a value for each pixel of the interference pattern captured by the imaging camera. The modulation is used to identify pixels associated with the edge of the lens. An ellipse is fit to the identified pixels and the center of the ellipse is determined. Using any appropriated (e.g., predetermined) mapping equation, the determined center, which represents the center of the lens as captured by the imaging camera, is mapped to the center of the science camera. The appropriate region of the interference pattern captured by the science camera is masked to leave the region of interest of the lens. The transmitted wavefront of this region of interest is computed for further analysis.

The various techniques described herein can be implemented in connection with hardware or software or, where appropriate, with a combination of both. Thus, the methods for the use of interferometry for transmitted wavefront testing of lenses, or certain aspects or portions thereof, can take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for the use of interferometry for transmitted wavefront testing of lenses.

The program(s) can be implemented in assembly or machine language, if desired. In any case, the language can be a compiled or interpreted language, and combined with hardware implementations. The methods for the use of interferometry for transmitted wavefront testing of lenses also can be practiced via communications embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, or the like, the machine becomes an apparatus for the use of interferometry for transmitted wavefront testing of lenses. When implemented on a general-purpose processor, the program code combines with the processor to provide a unique apparatus that operates to invoke the functionality the use of interferometry for transmitted wavefront testing of lenses. Additionally, any storage techniques used in connection with the use of interferometry for transmitted wavefront testing of lenses can invariably be a combination of hardware and software.

While the use of interferometry for transmitted wavefront testing of lenses has been described in connection with the example embodiments of the various figures, it is to be understood that other similar embodiments can be used or modifications and additions can be made to the described embodiments for performing the same functions for the use of interferometry for transmitted wavefront testing of lenses without deviating therefrom. Therefore, the use of interferometry for transmitted wavefront testing of lenses as described herein should not be limited to any single embodiment, but rather should be construed in breadth and scope in accordance with the appended claims.

What is claimed:

1. A cuvette configured to hold a plurality of ophthalmic lenses, the cuvette comprising:
a carousel comprising a plurality of cells, wherein:
each cell comprises
a tapered wall that is configured to conform to an ophthalmic lens submerged in a solution, and
at least one channel configured to allow solution to flow therethrough to at least one other cell;
and
the carousel is rotatable within the cuvette;
a first window configured to allow light to enter a cell;
a second window forming a surface of a cell opposite the first window, the second window configured to allow the light to exit a cell, wherein a cell is positionable to allow light to propagate through the first window and a second window via rotation of the carousel; and
an enclosure that is positioned around the carousel and is configured to prevent solution from leaking out of the cuvette.

2. The cuvette in accordance with claim 1, further comprising a coupling mechanism configured:
to kinematically couple the cuvette to an interferometer; and
allow rotation of the carousel via the interferometer.

3. The cuvette in accordance with claim 2, wherein the coupling mechanism comprises at least one pulley coupleable to a drive belt.

4. The cuvette in accordance with claim 3, wherein the coupling mechanism provides vibration isolation between the cuvette and the interferometer.

5. The cuvette in accordance with claim 2, the coupling mechanism further comprising:
a slide mechanism configured to provide:
coupling of the cuvette and the interferometer; and
initial alignment of cuvette and the interferometer.

6. The cuvette in accordance with claim 5, the cuvette further comprising:
a locator pin configured to locate the cuvette in a plane parallel to the slide mechanism; and;
a resilient arm coupled to the locator pin, the resilient arm configured to provide a radial force against the locator pin.

7. The cuvette in accordance 1 further comprising:
an intake portion in said enclosure configured to allow solution to enter the cuvette; and
a drain portion in said enclosure configured to allow solution to exit the cuvette.

8. The cuvette in accordance with claim 1, wherein the cuvette is configured to provide temperature stabilization of a solution therein.

9. The cuvette in accordance with claim 1, the cuvette further comprising a temperature probe configured to monitor a temperature of a solution therein.

10. The cuvette in accordance with claim 1, wherein the tapered wall is configured to facilitate placement of an ophthalmic lens in the cell without deformation of the lens placed in the cell.

11. The cuvette in accordance with claim 1, wherein the enclosure comprises polycarbonate.

12. The cuvette in accordance with claim 1, wherein the enclosure is opaque.

13. The cuvette in accordance with claim 1, wherein the solution comprises at least one of a saline solution, a buffered saline solution, de-ionized water, and a solution comprising an active pharmaceutical.

14. The cuvette in accordance with claim 1, wherein an ophthalmic lens positioned in a cell between the first window and the second window is visible in its entirety via the first window and the second window.

15. The cuvette in accordance with claim 1, wherein an ophthalmic lens is not deformed when positioned in a cell.

16. The cuvette in accordance with claim 1, wherein bubbles formed in the solution are not visible via the first window and the second window.

17. The cuvette in accordance with claim 1, wherein second windows of the plurality of cells are coplanar.

18. The cuvette in accordance with claim 1, wherein the first window and second window are configured to preserve a collimation and a coherence of light propagating therethrough.

19. The cuvette in accordance with claim 1, wherein the cuvette is configured to accommodate at least one ophthalmic lens selected from a group of ophthalmic lenses comprising: a hard contact lens, a hard refractive contact lens, a hard diffractive contact lens, a hard hybrid refractive/diffractive contact lens, a soft contact lens, a soft refractive contact lens, a soft diffractive contact lens, a soft hybrid refractive/diffractive contact lens, a hard contact lens comprising an active pharmaceutical, a soft contact lens comprising an active pharmaceutical, a single vision lens, a toric lens, a bifocal contact lens, a multifocal lens, a cosmetically tinted lens, a freeform lens, an intraocular lens, an intraocular refractive lens, an intraocular diffractive lens, an intraocular hybrid refractive/diffractive lens, an accommodating lens, a spectacle lens, a refractive spectacle lens, a diffractive spectacle lens, and a hybrid refractive/diffractive spectacle lens, a composite lens comprising a plurality of embedded materials, a photochromic lens, and a mold for fabrication of a lens.

* * * * *